(12) United States Patent
Gaudl et al.

(10) Patent No.: US 9,938,232 B2
(45) Date of Patent: *Apr. 10, 2018

(54) LED PHOTOINITIATORS

(71) Applicant: SUN CHEMICAL CORPORATION, Parsippany, NJ (US)

(72) Inventors: Kai-Uwe W. Gaudl, Bavaria (DE); Juergen Dieker, Hesse (DE)

(73) Assignee: SUN CHEMICAL CORPORATION, Parsippany, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/305,133

(22) PCT Filed: Apr. 17, 2015

(86) PCT No.: PCT/US2015/026427
§ 371 (c)(1),
(2) Date: Oct. 19, 2016

(87) PCT Pub. No.: WO2015/164208
PCT Pub. Date: Oct. 29, 2015

(65) Prior Publication Data
US 2017/0044093 A1    Feb. 16, 2017

Related U.S. Application Data

(60) Provisional application No. 61/983,166, filed on Apr. 23, 2014.

(51) Int. Cl.
*C08F 2/46* (2006.01)
*C08F 2/50* (2006.01)
(Continued)

(52) U.S. Cl.
CPC .............. *C07C 229/66* (2013.01); *C08F 2/50* (2013.01); *C09D 11/101* (2013.01); *C09D 133/08* (2013.01)

(58) Field of Classification Search
None
See application file for complete search history.

(56) References Cited

U.S. PATENT DOCUMENTS

| | | | |
|---|---|---|---|
| 4,022,674 A | 5/1977 | Rosen | |
| 4,431,840 A | 2/1984 | Sterken et al. | |

(Continued)

FOREIGN PATENT DOCUMENTS

| | | |
|---|---|---|
| DE | 27 09 580 A1 | 9/1977 |
| JP | 01 261355 A | 10/1989 |

(Continued)

OTHER PUBLICATIONS

Bhatt et al, Aspects of Tautomerism. 7. Study of Keto Patricipation in Alkaline Hyudrolysis of NOrmal Esters of gamma-keto-Acids, 1979, J. Org. Chem., vol. 44, No. 6, 984-989.*

(Continued)

*Primary Examiner* — Jessica Whiteley
(74) *Attorney, Agent, or Firm* — Charles C. Achkar; Ostrolenk Faber LLP.

(57) ABSTRACT

Amine derivatives of benzoylbenzoic acid, benzoylbenzoic acid esters and salts were prepared, which are suitable as photo initiators for UV & LED curable compositions. The derivatives are compounds of Formula I, Ia, and II wherein $R^1$, $R^{1a}$, $R^2$, $R^3$, n and r are as defined herein.

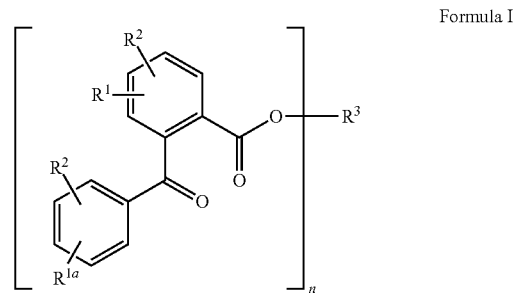

Formula I

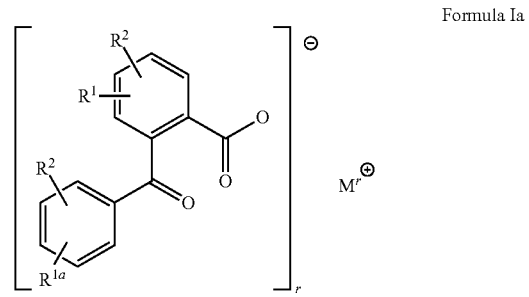

Formula Ia

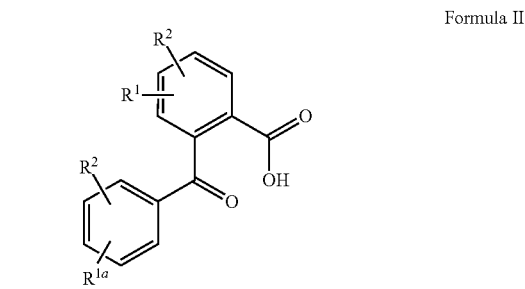

Formula II

15 Claims, 1 Drawing Sheet

(51) Int. Cl.
    *C08G 61/04*     (2006.01)
    *C07C 229/66*     (2006.01)
    *C09D 11/101*     (2014.01)
    *C09D 133/08*     (2006.01)

(56) References Cited

U.S. PATENT DOCUMENTS

| | | | |
|---|---|---|---|
| 2010/0143274 A1 | 6/2010 | Deshayes et al. | |
| 2016/0160061 A1* | 6/2016 | Gaudl | C08F 2/50 428/195.1 |

FOREIGN PATENT DOCUMENTS

| | | |
|---|---|---|
| JP | 05 119474 A | 5/1993 |
| WO | 2005/112932 A2 | 12/2005 |
| WO | 2008/061957 A1 | 5/2008 |
| WO | 2008/070737 A1 | 6/2008 |
| WO | 2015/023371 A1 | 2/2015 |

OTHER PUBLICATIONS

Notification Concerning Transmittal of the International Preliminary Report on Patentability (Chapter 1 of the Patent Cooperation Treaty) issued in International Application No. PCT/US2015/026427, dated Nov. 3, 2016.

PUBCHEM, Compound Summary CID 66628591, Create Date: Nov. 30, 2012. [retrieved on Jun. 11, 2015]. Retrieved from the Internet. <URL:https://pubchem.ncbi.nlm.nih.gov/compound/66628591?from=summary>.entire document.

PCT International Search Report issued in PCT/US2015/026427 dated Jul. 8, 2015.

Written Opinion of the International Searching Authority issued in PCT/US2015/026427 dated Jul. 8, 2015.

European Search Report issued in European Application No. 15 78 2816, dated Oct. 30, 2017.

* cited by examiner

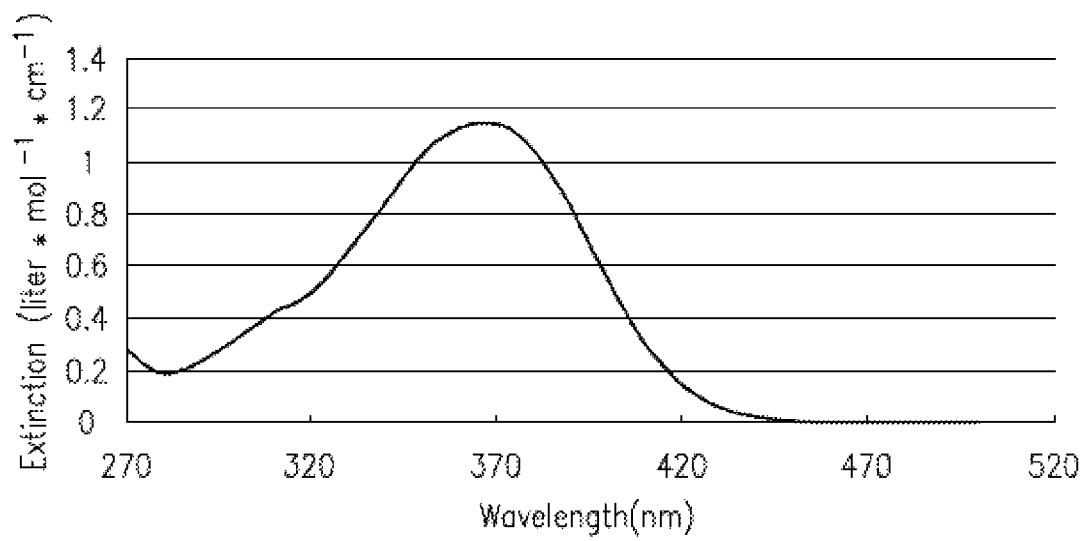

LED PHOTOINITIATORS

CROSS REFERENCE TO RELATED APPLICATIONS

The present application is a § 371 National Phase application based on PCT/US2015/026427 filed Apr. 17, 2015, which claims the benefit of U.S. Provisional Application No. 61/983,166, filed Apr. 23, 2014 the subject matter of each of which is incorporated by reference in their entirety.

FIELD OF THE INVENTION

The present invention relates to novel photoinitiators for radical energy curing systems, curable with UV-light emitted by light emitting diodes (LED).

BACKGROUND

Radiation curable compositions containing acrylic acid ester groups are mainly cured by exposure to ultraviolet light (UV). For a radiation curable composition, a photoinitiator is necessary, which forms radicals under irradiation with photons, and initiates free-radical polymerization, which then leads to a hardening (curing) of a liquid coating or ink.

In the last years, UV light emitting diodes (UV-LED) have become more attractive as the power output capabilities considerably increased for UV-LED's of wavelengths of 365-405 nm. The UV-LED bulbs do not generate ozone, in contrast to the typical UV-bulbs, require less energy, and exhibit a longer lifetime. Moreover, an additional advantage for UV-LED systems over the currently used UV-bulbs and UV-energy saving bulbs is the absence of mercury in the bulb. Therefore, UV-LED's are regarded as a "green" solution over typical mercury containing UV-bulbs.

Benzophenone derivatives (e.g. in CN103064251), or α-diketones such as camperquinone (in e.g. EP1245219) have been proposed as LED initiators. But the most widely used LED initiators are thioxanthone derivatives (e.g. in US2013176370) and acylphosphine oxide derivatives (e.g. in US2005234145).

In order to enable cure with UV-LED bulbs in a pigmented coating, such as a printing ink for example, ink makers typically increase the level of photoinitiators and sensitizers that absorb long wavelengths, such as acylphosphine or thioxanthone (TX) derivatives. Photoiniators that absorb long wavelengths are able to catch more light from UV-LED emissions, emitting at 365-405 nm, generating more radicals formed to promote curing of coatings and inks in depth, and especially on the surface. Surface curing is a challenge when using UV-LED, because short wavelengths irradiation is missing. Absorption of UV radiation of short wavelengths typically promotes surface cure.

However, using a high level of photoinitiators has the disadvantage that the ink or coating is filled with many small photoinitiator molecules which can migrate. Migration of small molecule photoinitiators causes concern about toxicology, odor, or off taste in food packaging applications.

Low molecular weight thioxanthone (TX) derivatives, such as isopropyl thioxanthone, tend to migrate and are reported to give unstable yellowing behavior (e.g. mentioned in WO2013/164394). Acyl phosphine oxide initiators can produce an odor, and because they are phosphor-organic compounds and type-I photoinitiators, can lead to splitting products. Splitting products can cause health and safety problems.

As a solution, higher molecular weight oligomeric and polymeric photoinitiators are proposed in the art to minimize migration in inks ["Industrial Photoinitiators", CRC press London 2010]. Commercially available materials are, for example, oligomeric thioxanthone derivatives such as Omnipol TX (IGM resin) and Genopol TX (Rahn group). The UV absorption of these materials matches the UV emission of the UV-LED bulbs at 365-395 nm. However, usually such thioxanthone materials are not solely able to form enough radicals under irradiation, and require additional synergists and co-initiators, such as benzophenones and amines, in order to be effective. The synergists and co-initiators must be low migration products as well, which makes the photoinitiator blend sophisticated and costly.

In the last decades, water-based UV-curable systems have become a growing field, as water can reduce viscosity of UV-curable compositions, which makes it attractive for UV-flexographic, UV-gravure, and UV-digital printing applications. Moreover, if water can replace a part of an organic material in a formulation, it makes the whole formulation more sustainable. However, there are very limited water-soluble materials described which can be used as LED photoinitiators. Usually only aqueous dispersions, such as Irgacure 819Dw (BASF company) are described in the prior art, and therefore there is a high demand for water-soluble LED photoinitiator materials.

Additionally, due to legislation initiatives to phase out mercury containing UV-bulbs in electric and electronic equipment, there is a strong need to develop new photoinitiators curable with UV-LED light, for environmentally friendly applications, such as, for example, low migration inks and water-based inks and coatings.

DE 2709580 (U.S. Pat. No. 4,323,700) describes a process for preparing benzophenone derivatives from 3-phenylphthalide derivatives with the use of at least one oxidizing agent.

U.S. Pat. No. 4,431,840 discloses substituted 2-benzoylbenzoic acids useful as intermediates for preparing chromogenic phthalide compounds.

CN 101747654 discloses a method of preparing benzofuran ketone compounds containing indoles as substituent groups. The compounds are useful as electronic supplying colorless dye, and can be used as thermal-pressure sensitive color couplers in the paper industry.

JP H07-196929 discloses phthalide compounds useful as an electron-donating leuco dye for recording material having a color-developing part.

US 2008/0196176 discloses leuco colorants for use as consumer product additives to indicate a product function by color change, make visual effects, or to provide latent or delayed color generation.

U.S. Pat. No. 4,535,172 discloses 3-aryl or heteroaryl-3-alkoxy-, phenoxy-, alkylthio-, or phenylthiophthalides useful as color formers.

WO 2013/164394 discloses substituted derivatives of alpha-di-ketones which can be used as photoinitiators in LED photocuring.

US 2013/0176370 discloses an LED radiation curable composition comprising a thioxanthone derivative as a diffusion-hindered photoinitiator.

Therefore, the object of the present invention is to address the aforementioned technical shortcomings, and provide photoinitiators that preferably absorb in the region between 365 nm and 420 nm, exhibiting high photochemical reactivity and good surface cure, have minimal odor or odorous splitting products, and have an increased molecular weight for a low risk of migration.

SUMMARY OF THE INVENTION

The present invention relates to novel amine derivatives of benzoylbenzoic acid, benzoylbenzoic acid esters, and salts thereof, photoinitiators that are suitable for use in radiation curable inks and coatings. More specifically, the invention relates to radical photoinitiators having absorption spectra at 365-405 nm, which are suitable for light emitting diodes (LED) curable compositions. In a second embodiment, the invention relates to water soluble LED photoinitiators.

In a particular aspect, the present invention provides a compound of Formula I:

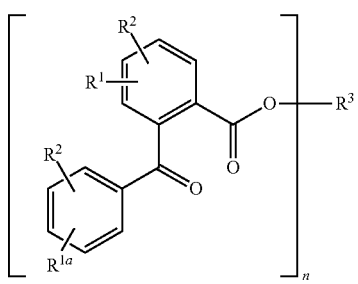

Formula I wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine;

Each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy;

$R^3$ is selected from the group consisting of a mono-, di-, tri-, tetra-, penta-, hexa-, or polyvalent alkyl or alkoxy radical, optionally substituted with one or more independently selected oxygen, sulfur, nitrogen, OH, carbonyl, (hydroxyl)alkyl, COOH, (carboxy)alkyl, $R^4$, carboxamido, (carboxamido)alkyl, or $OCONR^5$;

$R^4$ is selected from the group consisting of $C_3$-$C_{12}$ cycloalkyl, (cycloalkyl)alkyl, $C_6$-$C_{12}$ aryl, $C_3$-$C_{12}$ heterocycle, $C_6$-$C_{12}$ heteroaryl, aralkyl, and alkaryl, each of which is optionally substituted with one or more independently selected OH, (hydroxy)alkyl, $C_1$-$C_{12}$ alkyl, carboxamido, (carboxamido)alkyl, COOH, or (carboxy)alkyl;

$R^5$ is selected from the group consisting of H, $C_1$-$C_{12}$ alkyl, and $C_1$-$C_{12}$ alkoxy; and n denotes an integer from 1-100; provided that n is less than or equal to the valency of the alkyl or alkoxy radical of $R^3$.

In another aspect, the present invention provides a compound of Formula Ia:

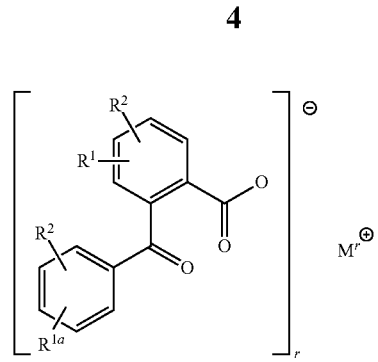

Formula Ia wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine;

Each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy;

r denotes an integer from 1-6;

M is selected from the group consisting of a mono-, di-, tri-, tetra-, penta- or hexavalent metal cation, a protonated tertiary amine, tetraalkyl ammonium group radical, phosphonium, sulfonium, and pyridinium, each of which can be optionally substituted by one or more $C_1$-$C_{12}$ alkyl radicals.

In yet another aspect, the present invention provides a use of a compound of Formula II as a photoinitiator:

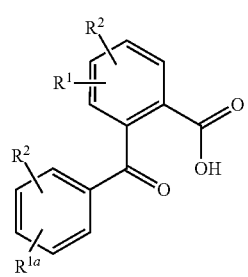

Formula II wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine; and each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy.

In a certain embodiment of any one of Formula I, Ia, or II, $R^1$ and $R^{1a}$ are each an independently selected tertiary amine.

In a certain embodiment, the present invention provides a UV-curable ink or coating composition comprising at least one acrylate or methacrylate compound and at least one compound of Formula I, Ia or II.

In another embodiment, the UV-curable ink or coating composition further comprises at least one colorant.

In a certain embodiment, the present invention provides an aqueous UV-curable ink or coating composition comprising at least one acrylate or methacrylate compound, water, and at least one compound of Formula Ia.

In another embodiment, the aqueous UV-curable ink or coating composition further comprises at least one colorant.

In a certain embodiment, the present invention provides a UV-curable ink or coating composition comprising at least one acrylate or methacrylate compound, and at least one compound of Formula I, Ia, or II, and optionally further comprising a colorant, that is curable with light having a wavelength maximum of 300 to 450 nm, such as that emitted by LED modules.

In a certain embodiment, the present invention provides an aqueous UV-curable ink or coating composition comprising at least one acrylate or methacrylate compound, water, and at least one compound of Formula Ia, and optionally further comprising a colorant, that is curable with light having a wavelength maximum of 300 to 450 nm, such as that emitted by LED modules.

In a certain embodiment, the present invention provides a UV-curable ink or coating composition comprising at least one acrylate or methacrylate compound, and at least one compound of Formula I, Ia, or II, and optionally further comprising a colorant, that is curable with light having a wavelength maximum of 350 to 450 nm, such as that emitted by LED modules.

In a certain embodiment, the present invention provides an aqueous UV-curable ink or coating composition comprising at least one acrylate or methacrylate compound, water and at least one compound of Formula Ia, and optionally further comprising a colorant, that is curable with light having a wavelength maximum of 350 to 450 nm, such as that emitted by LED modules.

In a certain embodiment, the present invention provides the use of an ester, thioester, urethane, or amide linked compound of Formula II as a UV-photoinitiator absorbing wavelengths in a range of 300-450 nm in a UV curable ink or coating composition.

In another embodiment, the present invention provides the use of an ester, thioester, urethane, or amide linked compound of Formula II as a UV-photoinitiator absorbing wavelengths in a range of 350-450 nm in a UV curable ink or coating composition.

BRIEF DESCRIPTION OF THE DRAWINGS

FIG. 1: FIG. 1 is the UV-VIS absorption spectrum of the potassium salt of 5-(dimethylamino)-2-[4-dimethylamino] benzoylbenzoic acid (Example 6) in water at a concentration of 0.01 g/L.

DETAILED DESCRIPTION OF THE INVENTION

It is to be understood that the foregoing general description and the following detailed description are exemplary and explanatory only, and are not restrictive of any subject matter claimed.

Unless otherwise defined, all technical and scientific terms used herein have the same meaning as is commonly understood by one of skill in the art to which the inventions belong. All patents, patent applications, published applications and publications, websites and other published materials referred to throughout the entire disclosure herein, unless noted otherwise, are incorporated by reference in their entirety for any purpose.

In this application, the use of the singular includes the plural unless specifically stated otherwise. As used herein, the singular forms "a," "an" and "the" are intended to include the plural forms as well, unless the context clearly indicates otherwise.

In this application, the use of "or" means "and/or" unless stated otherwise.

As used herein, the terms "comprises" and/or "comprising" specify the presence of the stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "composed," "comprised" or variants thereof are used in either the detailed description or the claims, such terms are intended to be inclusive in a manner similar to the term "comprising."

As used herein, ranges and amounts can be expressed as "about" a particular value or range. "About" is intended to also include the exact amount. Hence "about 5 percent" means "about 5 percent" and also "5 percent." "About" means within typical experimental error for the application or purpose intended.

As used herein, the terms "(meth)acrylate" or "(meth) acrylic acid" include both acrylate and methacrylate compounds.

Throughout this disclosure, all parts and percentages are by weight (wt % or mass % based on the total weight) and all temperatures are in ° C. unless otherwise indicated.

As used herein, the term "alkyl" refers to straight chain and branched saturated non-cyclic hydrocarbons, having from 1 to 20 carbon atoms. Representative straight chain alkyl groups include methyl, -ethyl, -n-propyl, -n-butyl, -n-pentyl, -n-hexyl, n-heptyl, n-octyl, n-nonyl, n-decyl, and n-amyl. Representative branched alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 5-methylhexyl, 6-methylheptyl, 2-ethylhexyl, and the like.

As used herein, the term "alkoxy" means a straight chain or branched non-cyclic hydrocarbon having one or more ether groups and from 1 to 20 carbon atoms. Representative straight chain and branched alkoxys include -methoxy, -ethoxy, -propoxy, -butyloxy, -pentyloxy, -hexyloxy, -methoxymethyl, -2-methoxyethyl, -5-methoxypentyl, -3-ethoxybutyl and the like.

As used herein, the term "amine" refers to an ammonia derivative wherein one, two or three hydrogen atoms have been replaced by an organic substituent.

As used herein, the term "tertiary amine" refers to an amine in which all three hydrogen atoms have been replaced by organic substituents. Examples of suitable organic substituents are alkyl and aryl.

As used herein the term "protonated tertiary amine" is a tertiary amine which, when dissolved in an organic solvent and treated with dilute aqueous acid, gains a hydrogen atom (proton) and becomes positively charged. Protonated tertiary amines are soluble in aqueous solvents as ammonium salts.

As used herein, the term "tetraalkyl ammonium group" is an amine substituted by four alkyl groups, which is permanently positively charged, independent of the pH of their solution.

As used herein, the term "amino" refers to —$NH_2$.

As used herein, the term "amide" is a derivative of an oxoacid in which an acidic hydroxyl group has been replaced by an amino or substituted amino group.

As used herein, the term "carboxamido" as used by itself or part of another group refers to a radical of formula —(C=O)$NR^aR^b$ or $R^aR^bN$(C=O)$OR^c$, wherein $R^a$, $R^b$, and $R^c$ are each independently selected hydrogen or optionally substituted alkyl. Examples of carboxamido groups include, but are not limited to, urethane, $CONH_2$, CON(H)$CH_3$, and CON($CH_3$)$_2$.

As used herein, the term "(carboxamido)alkyl" as used by itself or as part of another group refers to any of the above-mentioned alkyl groups substituted with a carboxamido group. Examples of (carboxamido)alkyl groups include, but are not limited to, —$CH_2CONH_2$, C(H)$CH_3CONH_2$, and $CH_2$CON(H)$CH_3$.

As used herein, the term "carboxy" as used by itself or as part of another group refers to the radical —COOH.

As used herein, the term "(carboxy)alkyl" as used by itself or as part of another group refers to any of the above-mentioned alkyl groups substituted with a —COOH.

As used herein, the term "(hydroxy)alkyl" as used by itself or as part of another group refers to an alkyl group as defined above substituted with one or more, e.g., one, two, or three, hydroxy groups. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

As used herein, the term "cycloalkyl" as used by itself or as part of another group refers to saturated and partially unsaturated (e.g. containing one or two double bonds) cyclic aliphatic hydrocarbons containing one to three rings having from three to twelve carbon atoms (i.e., $C_3$-$C_{12}$ cycloalkyl) or the number of carbons designated. In one embodiment, the cycloalkyl group has two rings. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and the like.

As used herein, the term "heterocycle" or "heterocyclo" refers to a 3- to 12-membered monocyclic heterocyclic ring which is either unsaturated or partially saturated. A 3-membered heterocycle can contain up to 1 heteroatom; a 4-membered heterocycle can contain up to 2 heteroatoms; a 5-membered heterocycle can contain up to 4 heteroatoms; a 6-membered heterocycle can contain up to 4 heteroatoms; and a 7-membered heterocycle can contain up to 5 heteroatoms. Each heteroatom is independently selected from nitrogen (which can be quaternized), oxygen, and sulfur (including sulfoxide and sulfone). The heterocycle can be attached via a nitrogen or carbon atom. Representative heterocycles include thiazolidinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiopyranyl, and the like.

As used herein, the term "aryl" means an aromatic carbocyclic ring containing 6 to 12 carbon atoms, including both mono-, bi-, and tricyclic ring systems. Representative aryl groups include -indenyl, -phenyl, -naphthyl and the like.

As used herein, "heteroaryl" means an aromatic heterocycle ring of 6- to 12-members, including both mono- and bicyclic ring systems, where at least one carbon atom (of one or both of the rings) is replaced with a heteroatom independently selected from nitrogen, oxygen, and sulfur, or at least two carbon atoms of one or both of the rings are replaced with a heteroatom independently selected from nitrogen, oxygen, and sulfur. Representative heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, thiadiazolyl, cinnolinyl, phthalazinyl, quinazolinyl, and the like.

As used herein, the phrase "optionally substituted" refers to a group that is either unsubstituted or substituted.

The present invention relates to novel amine derivatives of benzoylbenzoic acid, benzoylbenzoic acid esters, and salts thereof, as photoinitiators that are suitable for radiation curable inks and coatings. More specifically, the invention relates to radical photoinitiators having an absorption spectrum at 365-405 nm, which are suitable for light emitting diodes (LED) curable compositions. In a second embodiment, the invention relates to water soluble LED photoinitiators. The present invention further relates to radical photoinitiator compositions, absorbing light between 365-405 nm, comprising the novel amine derivatives of benzoylbenzoic acid, benzoylbenzoic acid esters, and salts thereof, that are suitable to cure energy-curable compositions with light-emitting diodes (LED).

The Inventors observed that photoinitiators of Formula I, Ia, or II are suitable to cure UV-curable inks and coatings with LED light having wavelengths of 300-450 nm, more preferably 350-450.

In a particular aspect, the present invention provides a compound of Formula I:

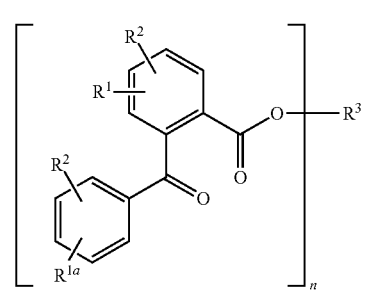

Formula I wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine;
Each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy;

$R^3$ is selected from the group consisting of a mono-, di-, tri-, tetra-, penta-, hexa-, or polyvalent alkyl or alkoxy radical, optionally substituted with one or more independently selected oxygen, sulfur, nitrogen, OH, carbonyl, (hydroxyl)alkyl, COOH, (carboxy)alkyl, $R^4$, carboxamido, (carboxamido)alkyl, or $OCONR^5$;

$R^4$ is selected from the group consisting of $C_3$-$C_{12}$ cycloalkyl, (cycloalkyl)alkyl, $C_6$-$C_{12}$ aryl, $C_3$-$C_{12}$ heterocycle, $C_6$-$C_{12}$ heteroaryl, aralkyl, and alkaryl, each of which is optionally substituted with one or more independently selected OH, (hydroxy)alkyl, $C_1$-$C_{12}$ alkyl, carboxamido, (carboxamido)alkyl, COOH, or (carboxy)alkyl;

$R^5$ is selected from the group consisting of H, $C_1$-$C_{12}$ alkyl, and $C_1$-$C_{12}$ alkoxy; and n denotes an integer from 1-100; provided that n is less than or equal to the valency of the alkyl or alkoxy radical of $R^3$.

In another aspect, the present invention provides a compound of Formula Ia:

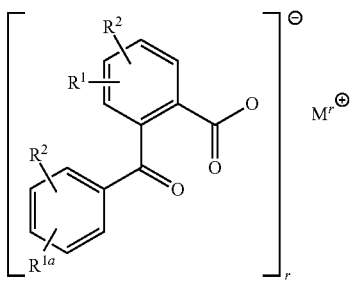

Formula Ia wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine;

Each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy;

r denotes an integer from 1-6;

M is selected from the group consisting of a mono-, di-, tri-, tetra-, penta- or hexavalent metal cation, a protonated tertiary amine, tetraalkyl ammonium group radical, phosphonium, sulfonium, and pyridinium, each of which can be optionally substituted by one or more $C_1$-$C_{12}$ alkyl radicals.

In yet another aspect, the present invention provides use of a compound of Formula II as a photoinitiator:

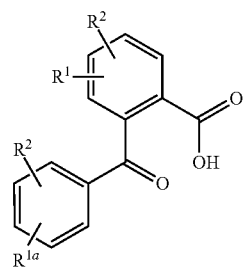

Formula II wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine; and each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy.

The compounds of Formula I can be made, for example, by a condensation reaction of an aromatic aldehyde with an aminobenzoic acid followed by oxidation and esterification with an alcohol.

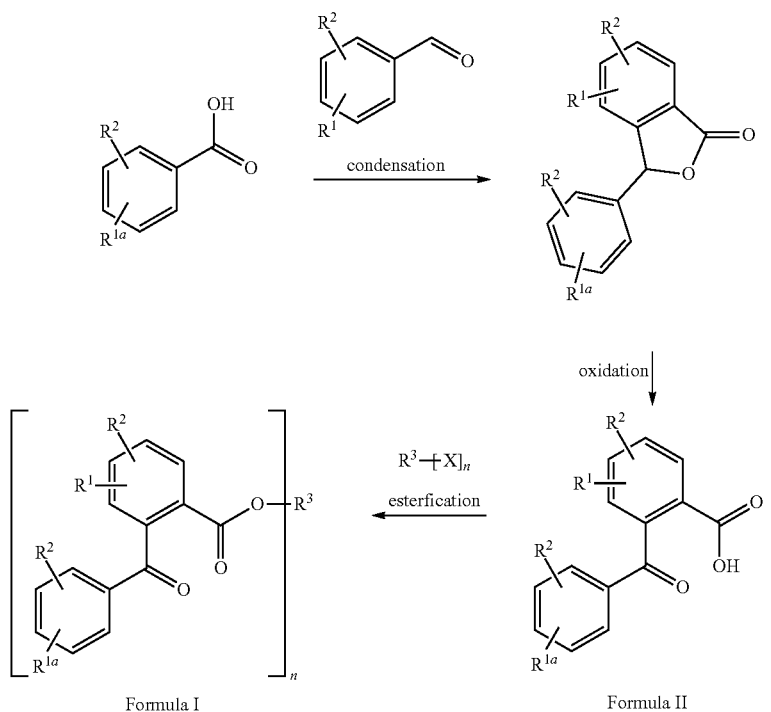

wherein X is typically OH and n is 1 to 100 dependent on the valency of the alcohol.

Alternatively, the esterification in the last step can be done for example with an epoxide or a carbodiimide.

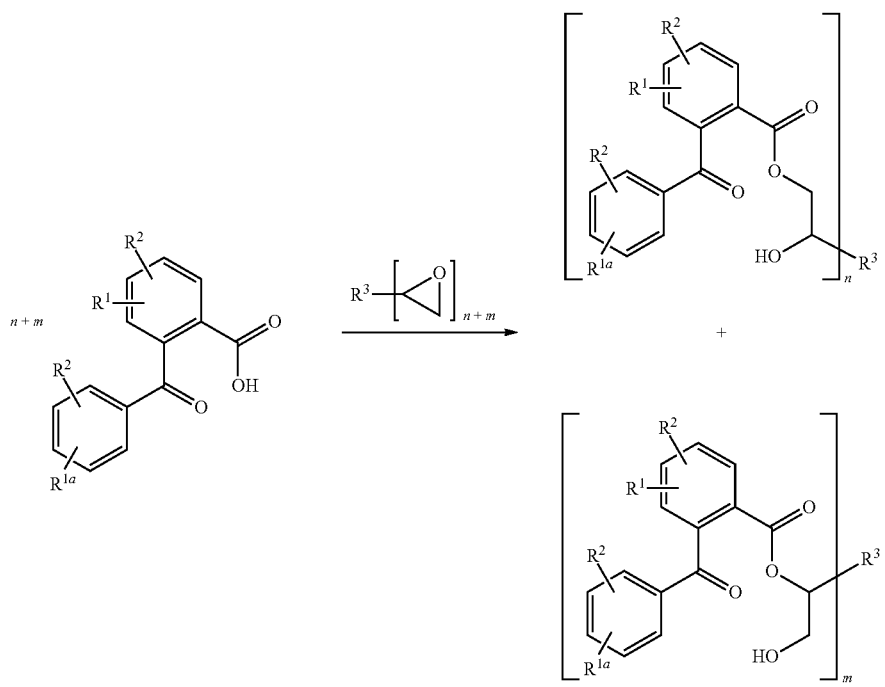

The first step, the synthesis of phenylphthalides, is described for example in DE2709580. Such materials can be made from an amine substituted benzaldehyde derivative and benzoic acid derivatives by condensation in high yields greater than 80%.

In the second step, compounds of Formula II can be made by dispersing or dissolving the phthalides into an aqueous solution of alkali salt and oxidizing with the use of at least one oxidizing agent, such as, for example, CuO, $CeO_2$, $FeCl_3$, peracetic acid, nitro-compounds or hypochlorites, at a temperature of 0-200° C., for the period of between several minutes and several hours to obtain the compounds of Formula II. An aqueous solution of a metal salt is preferred as the alkali salt. The compounds of Formula II are subsequently esterified as described in the depicted aforementioned reaction scheme, and described hereinafter, and give the compounds of Formula I.

Alternatively, the compounds of Formula I can be made, for example, by a Friedel-Crafts acylation of aromatic amines with anhydrides or acid chlorides, followed by esterification with an alcohol.

The compounds of Formula II are slightly pale yellow to faint greenish solids which are soluble in alkaline water. This offers also the possibility to purify the intermediate acids by dissolving in alkaline water and precipitation by acidification with an acid such as diluted sulfuric acid. Due to the possibility of an internal salt formation of carboxylic acid and amine groups, solubility of compounds of Formula II in organic solvents can be limited.

We observed that compounds of Formula II, which are described in the literature as building blocks for leuco-colorants and pressure sensitive recording materials (e.g. in CN 101747654, JP 07196929, US 2008/0196176 and U.S. Pat. No. 4,535,172), can also be used as radical photoinitiators.

The inventors have surprisingly discovered that compounds of Formula II are suitable as UV-LED light pho-

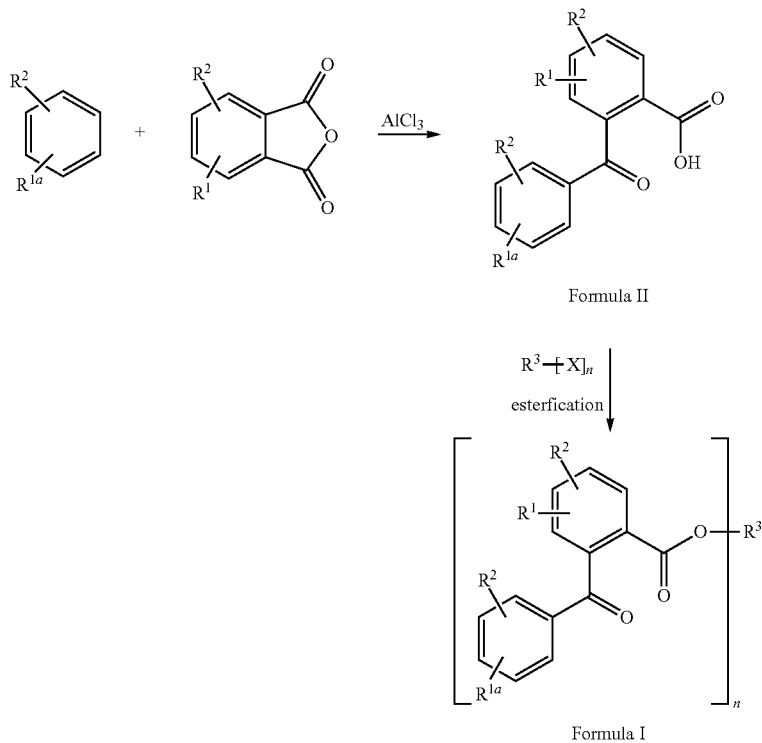

Formula II

Formula I wherein X is typically OH and n is 1 to 100 dependent on the valency of the alcohol.

This method requires fewer steps, but the Friedl-Crafts acylation requires special equipment, such as acid resistance reactors. General methods of acylation are described in the literature (Organikum, Wiley-VHC, $22^{nd}$ edition, page 380). Usually, aromatic amine and anhydride, and an optional solvent, are dissolved in each other, and aluminum trichloride is added so that the temperature does not exceed room temperature. Then the reaction is allowed to complete, and the mixture is poured into acidified water. Then the precipitated solid is collected, filtered, washed, and dried. The final esterification is done as described aforementioned in the reaction scheme and explained hereinafter.

A third method to make compounds of Formula II is described in U.S. Pat. No. 4,431,840. Here, leuco-colorants, such as crystal violet lactone, are hydrolyzed to give for example 5-(dimethylamino)-2-[4-dimethylamino] benzoyl-benzoic acid.

toinitiators. Among the materials described in the literature, those that are suitable contain at least one tertiary amine group and at least another electron donation group, such as, for example, an alkyl-, alkoxy- or amine group, which together shift the absorption maximum bathochromic to match with the emission of the UV-LED bulbs, emitting at wavelengths of preferably 300-450 nm, more preferably 350-450, most preferably 365-405 nm. Those materials, which are suitable as UV-LED photo initiators, that are defined by Formula II, include for example:
5-(methyl)-2-[4-dimethylamino] benzoylbenzoic acid;
5-(diethylamino)-2-[4-methyl] benzoylbenzoic acid;
5-(diethylamino)-2-[2-methoxy] benzoylbenzoic acid;
5-(ethoxy)-2-[4-dimethylamino] benzoylbenzoic acid;
5-(dimethylamino)-2-[4-dimethylamino] benzoylbenzoic acid;
5-(dimethylamino)-2-[2-dimethylamino] benzoylbenzoic acid;
5-(diethylamino)-2-[4-diethylamino] benzoylbenzoic acid;

5-(diethylamino)-2-[2-diethylamino] benzoylbenzoic acid;
5-(dipropylamino)-2-[4-dipropylamino] benzoylbenzoic acid;
5-(morpholino)-2-[4-dimethylamino] benzoylbenzoic acid;
5-(morpholino)-2-[4-morpholino] benzoylbenzoic acid;
5-(dimethylamino)-2-[4-methoxy] benzoylbenzoic acid;
5-(ethoxy)-2-[4-dimethylamino] benzoylbenzoic acid;
5-(aminomethylphenyl)-2-[4-dimethylamino] benzoylbenzoic acid;
5-(dimethylamino)-2-[4-methylphenylamino] benzoylbenzoic acid;
5-(dimethylamino)-2-[4-dimethylamino] benzoylbenzoic acid;
5-(dimethylamino)-2-[4-methoxyphenyl] benzoylbenzoic acid;
5-(ethoxy)-2-[4-dimethylamino-2-methoxy] benzoylbenzoic acid;
5-(dimethylamino)-2-[4-dimethylamino-2-methoxy] benzoylbenzoic acid;
5-(dimethylamino)-2-[4-methyl-2-methoxy] benzoylbenzoic acid;
5-(dimethylamino)-2-[4-dimetylamino-2-methoxy] benzoylbenzoic acid; and
5-(dimethylamino-3-methyl)-2-[4-methoxy-2-methoxy] benzoylbenzoic acid.

Moreover, for several applications, for example to improve solubility and increase molecular weight for low migration applications, it is preferable that compounds of the Formula II are esterified and become the inventive compounds of Formula I.

As mentioned above, radiation curable compositions containing small photoinitiators can be a challenge for several applications in packaging, especially in food packaging ("Radiation curing in packaging", Radtech Report March/April 2006). As described in the literature (L. L. Katan in "Migration of additive food contact", Black Academical & Professional, first edition, London 1996, page 97, table 5.3), the ability of a material to migrate is governed by its molecular weight rather than by its chemical structure. Thus, for a low migration UV-curable ink or coating, photoactive components having a molecular weight of greater than 500-1000 Daltons are preferred.

As a solution, the compounds of Formula II are preferably esterified with mono- and multifunctional alcohols to increase molecular weight for a lower migration risk and to increase solubility.

The compounds of Formula II can be used as photoinitiators as they are; however, it is advantageous to process them into a compound of Formula I. The Inventors observed that, without being bound to theory, once the acid group is esterified, a possible "internal salt" between amine group and acid group is no longer possible, which strongly increases solubility in organic materials such as acrylate and methacrylate monomers, which are widely used in radiation curable compositions.

Typically, compounds of Formula II can be esterified with alcohols, preferably with mono-, di-, tri-, tetra-, penta-, hexa- or polyvalent polyols such as methanol, ethanol, propanol, butanol, pentanol, hexanol, 2-ethylhexanol, octanol, ethylene glycol, 1,4-butandiol, 1,6-hexandiol, dipropylene glycol, neopentylglycol, diethylene glycol, triethylene glycol, tetraethylene glycol, ethoxylated neopentylglycol, propoxylated neopentylglycol, tripropylene glycol, ethoxylated bisphenol-A, poly(ethylene)glycol, trimethylolpropane, ethoxylated trimethylolpropane, propoxylated trimethylolpropane, propoxylated glycerol, pentaerythritol, ethoxylated pentaerythritol, propoxylated pentaerythritol, ethoxylated pentaerythritol, ditrimethylolpropane, dipentaerythritol, polyethylene glycols, polypropylene glycol, polytetrahydrofuran or mixtures thereof, preferred are ethoxylated trimethylolpropanes, ethoxylated pentaerythritols, propoxylated pentaerythritol and sugars such as sorbitol. Moreover, polymeric polyols such a poly etherpolyol, a polyesterpolyol, a hydroxyfunctional polyacrylate or the like can be used.

Usually, an acid catalyst, such as methane sulfonic acid or sulfuric acid, or a metal catalyst, such as titanium tetrabutylate or butyl tin hydroxyl-oxide, is suitable at a level of 0.1 to 5.0 weight %. The formed water can be removed physically by the help of an entrainer such as xylene, a nitrogen gas stream or vacuum.

Alternatively, for low reactive compounds of Formula II, they can be activated by making an acid chloride with, for example, thionyl chloride and esterified under milder conditions.

Alternatively, esterification can also be done with an epoxide. Suitable epoxides are, for example, glycidyl ethers, such as methyl glycidylether, allyl glycidylether, butyl glycidylether, 2-ethylhexyl glycidylether, stearyl glycidylether, cetyl glycidylether, phenyl glycidylether, biphenyl glycidylether, ethoxylated phenyl glycidylether, propoxylated phenyl glycidylether, and glycidylesters such as glycidyl acetate, glycidyl butyrate, glycidyl benzoate, Cadura E10 (Trade name), glycidyl phthalimide, resorcinol diglycidylether, hydroquinone diglycidylether, cyclohexane dimethanol diglycidylether, neopentyl glycol diglycidylether, hexane diol diglycidylether, adipic acid diglycidylether, terephthalic acid diglycidylether, phthalic acid diglycidylether, isophthalic acid diglycidylether, bisphenol A-diglycidyl ether, hydrogenated bisphenol A-diglycidyl ether, bisphenol S-diglycidyl ether, polyethylene glycol diglycidylethers, polypropylene glycol diglycidylethers, glycerol di- and triglycidyl ethers, trimethylol propane triglycidylether, pentaerythritol tetraglycidylether, sorbate hexaglycidylether, epoxidzed phenolic novolac, epoxidized cresol novolac or an acrylic copolymer with glycidyl methacrylate, or epoxidized oils such as epoxidized linseed oils and epoxidized castor oils, epoxidized alkyd resins, or epoxidized unsaturated hydrocarbons such as octyloxirane and cyclooctadiene diepoxide.

Usually, the reaction of epoxide and acid is catalyzed with, for example, phosphines such as triphenylphosphine, or a quarternary ammonium salt, such as tetraethylammonium chloride, or an imidazole compound. The reaction preferably proceeds at 25-180° C., more preferably at 90-130° C., with 0.1-2.0 weight % of catalyst. Especially for lower reactive acids, this is the preferred way to esterify the compounds of Formula II. As the epoxide group can be opened in two ways, usually a mixture of compounds is formed. Opening of epoxide always results in a hydroxyl-group which can be further functionalized.

One approach for the synthesis of a low migration LED-photoinitiator according to the present invention uses this hydroxyl-functionality to further increase molecular weight by reaction of the hydroxyl-functionality in Formula I obtained by reaction with an epoxide with isocyanates.

As isocyanates, any kind of isocyanate may be used. Difunctional isocyanates are preferred. As difunctional isocyanate compound, an aromatic isocyanate, alicyclic isocyanate, aliphatic isocyanate, and the like can be used. As examples of the aromatic diisocyanate, 2,4-tolylene diisocyanate, 2,6-tolylene diisocyanate, 1,3-xylylene diisocyanate, 1,4-xylylene diisocyanate, 1,5-naphthalene diisocyanate, m-phenylene diisocyanate, p-phenylene diisocyanate, 3,3'-dimethyl-4,4'-diphenylmethane diisocyanate, 4,4'-diphenylmethane diisocyanate, 3,3'-dimethylphenylene diisocyanate, 4,4'-biphenylene diisocyanate, bis(2-isocyanateethyl)fumarate, 6-isopropyl-1,3-phenyl diisocyanate, 4-diphenylpropane diisocyanate, tetramethylxylylene diisocyanate, and the like can be given. Examples of the alicyclic diisocyanate include isophorone diisocyanate, methylenebis (4-cyclohexylisocyanate), hydrogenated diphenylmethane diisocyanate, hydrogenated xylylene diisocyanate, 2,5-bis (isocyanatemethyl)-bicyclo[2.2.1]heptane, 2,6-bis(isocyanatemethyl)-bicyclo[2.2.1]heptane, and the like. As examples of the aliphatic diisocyanate, 1,6-hexane diisocyanate, 2,2,4-trimethylhexamethylene diisocyanate, and lysine diisocyanate. Of these, 1,6-hexane diisocyanate, 2,4-tolylene diisocyanate, isophorone diisocyanate, xylylene diisocyanate, and methylenebis(4-cyclohexylisocyanate) are preferable.

Furthermore, an isocyanate component having additional functional groups and/or additional isocyanate groups (such as tri-isocyanates or dimers or trimers or biuret derivatives of diisocyanates) may be used. Examples are the biuret of HDI (hexamethylenediisocyanate),

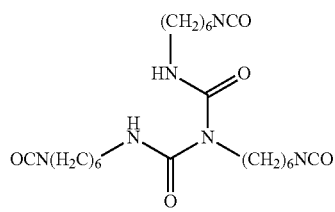

biuret of IPDI (isophorone diisocyanate), the trimer of HDI or the trimer of IPDI. According to the present invention, preferred trifunctional isocyanate compounds are the following commercially available materials: Tolonate HDT-LV, Tolonate HDT-LV2, Tolonate HDB-LV (all from Rhodia), Desmodur XP 2410, Desmodur N3600 or Desmodur N3200 (all from Bayer).

Modifying compounds may be attached to free functional groups of those isocyanate derivatives. For example, the attachment of a fatty acid (such as stearic acid) or a fatty alcohol (such as tridecanol) to a remaining isocyanate functionality results, after the reaction of one or two isocyanate-functions with the hydroxyl-functionality of a compound of Formula I. This may lead to a polyurethane with PI-functionality which in addition provides improved pigment wetting. Other modifying components may be attached as well.

Synthesis of a polyurethane from isocyanate and an alcohol is well-known in the art. Usually, the starting materials are added together into a reaction flask, and although no catalyst may be used, in a preferred embodiment a catalyst such as dibutyl tin dilaurate, bismuth carboxylate, basic amines like 1,4-diazabicyclo[2.2.2]octan (DABCO) or a zirconium chelate is added and the reaction mixture is heated to about 45 to 85° C., preferably 65 to 75° C., for a time sufficient for the reaction to take place, for example from 15 minutes to 3 hours. Depending on the starting materials, the exothermic reaction that occurs in the mixture is so pronounced that the temperature should be kept under a certain limit, for example under 70° C.

According to the present invention, a slight excess of hydroxy-functionality over isocyanate is used. Typically, a ratio OH:NCO of 2:1 to 1.01:1, preferably 1.5:1.1, is used.

However, in a further embodiment the isocyanate is used in a slight surplus, e.g. to make sure that all hydroxyl-functions of the compound of Formula I obtained after reaction with an epoxide are reacted. In this case, remaining isocyanate groups are converted by addition of an alcohol such as a polyol e.g. polyethylene glycols.

According to the present invention, the resulting polyurethane resin has a molecular weight in the range of 800 Dalton to 12,000 Dalton, preferably 1000 Dalton to 10,000 Dalton.

Alternatively, compounds of Formula II can be reacted with an oligomeric carbodiimide such as Carbodilite V-04 from Nishimbo Company Japan. Carbodiimides react with carboxylic acids under mild conditions without catalyst.

Alternatively, the ester group can be exchanged by a thioester group or amide group by reaction with a thiol, thiirane, or amine.

The compounds of Formula I are high viscosity, pasty to solid, yellow to brownish materials having a molecular weight of 500 to 5,000 Daltons, having an absorption maximum of 355-385 nm, and a molar extinction coefficient of 25000-40000 liter*mol$^{-1}$*cm$^{-1}$.

Examples of compounds of Formula I include, but are not limited to, the following:

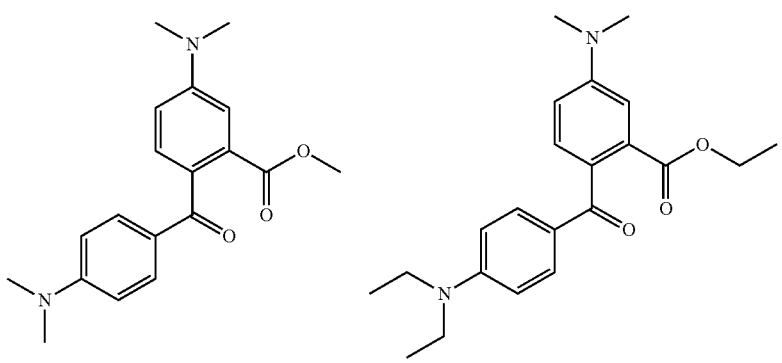

-continued
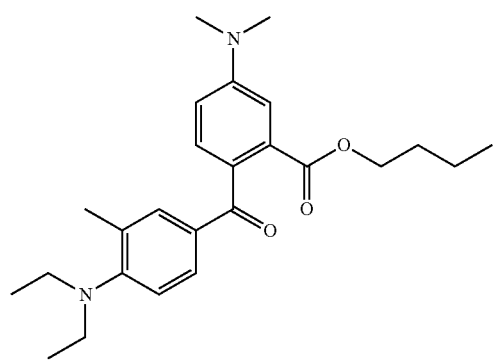
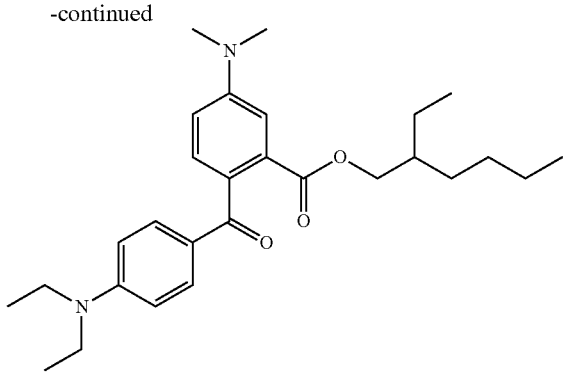
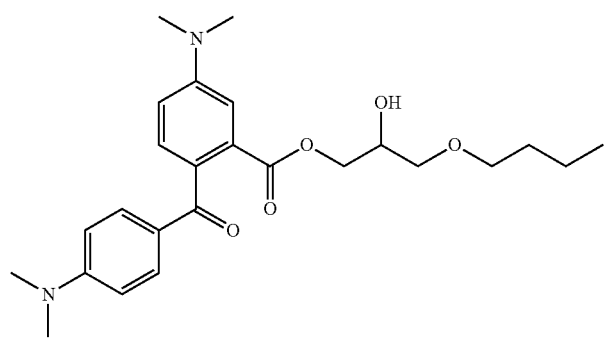
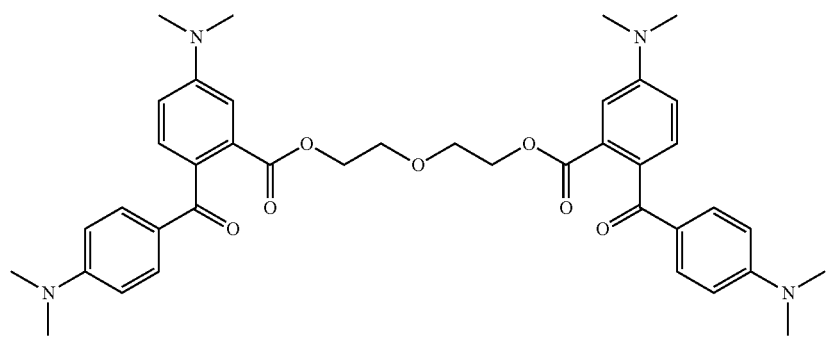
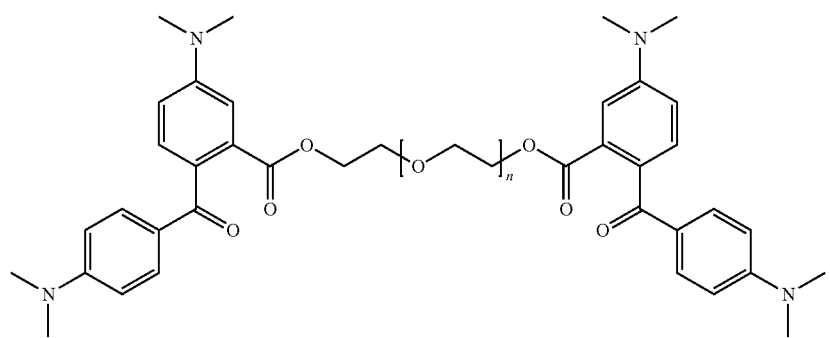

-continued
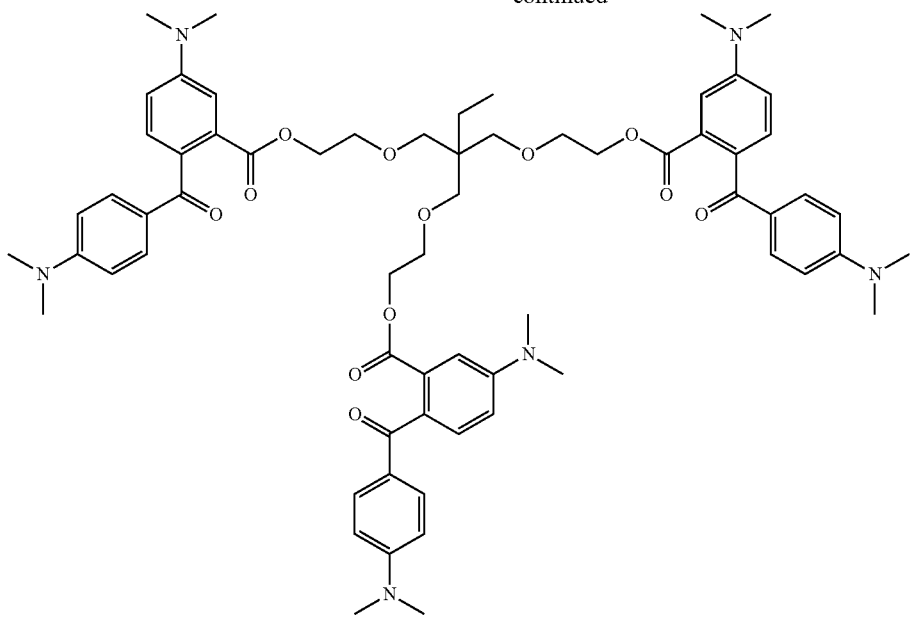
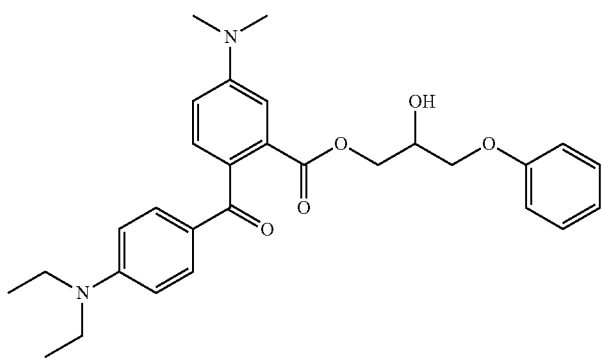
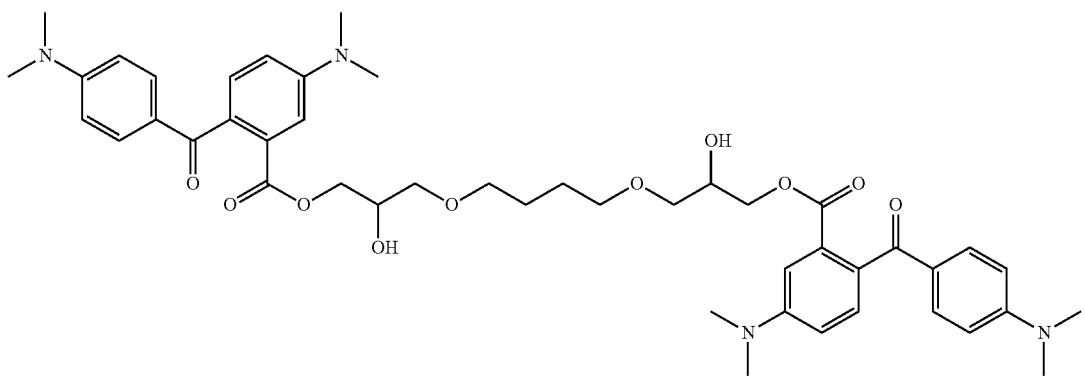

-continued
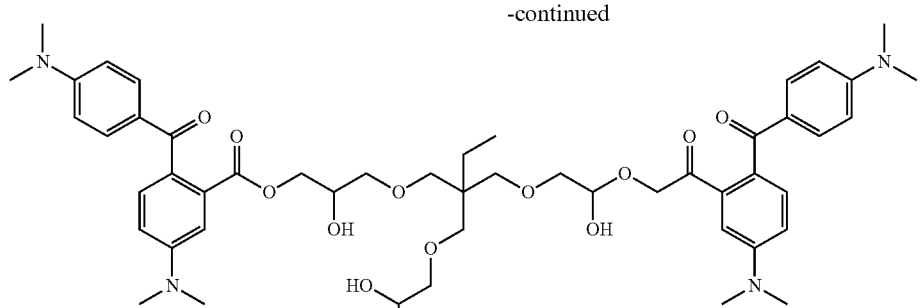
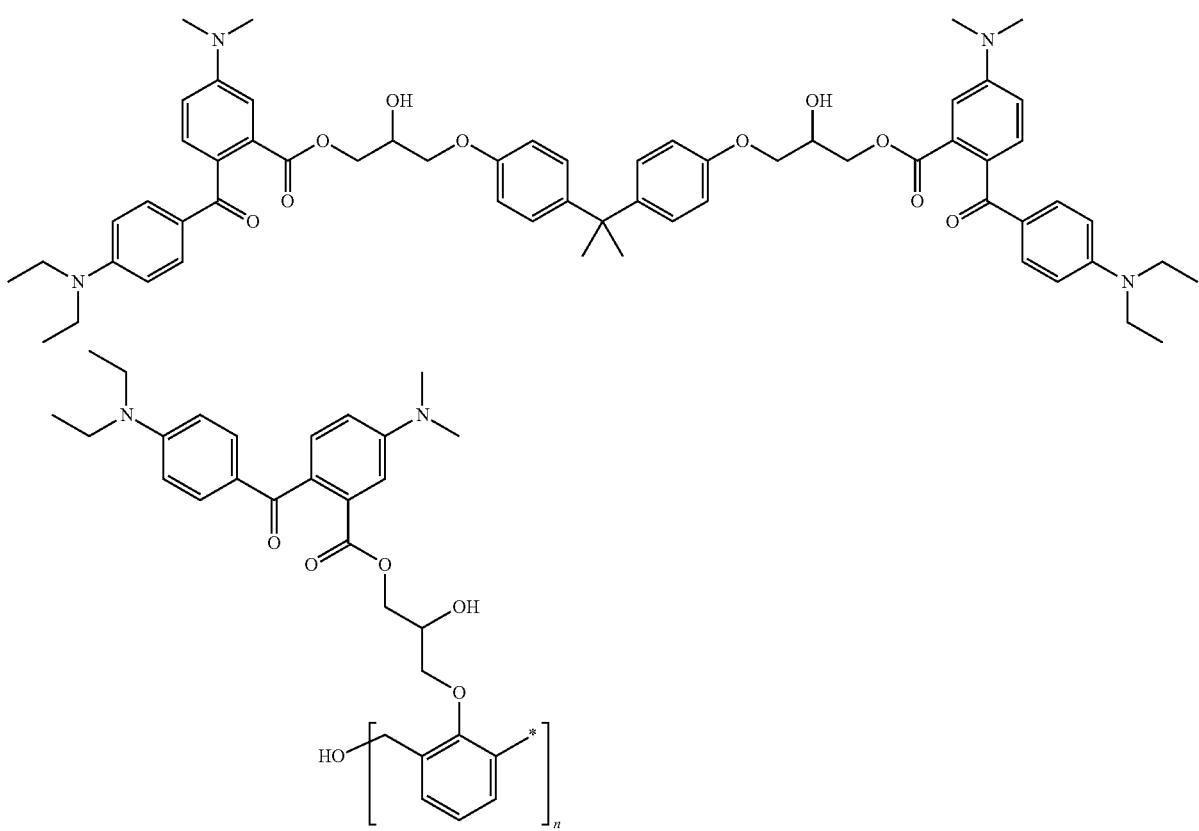
An example for a compound further modified by reaction with di-isocyanate (here hexamethylene-diisocyanate) is illustrated by the formula below:

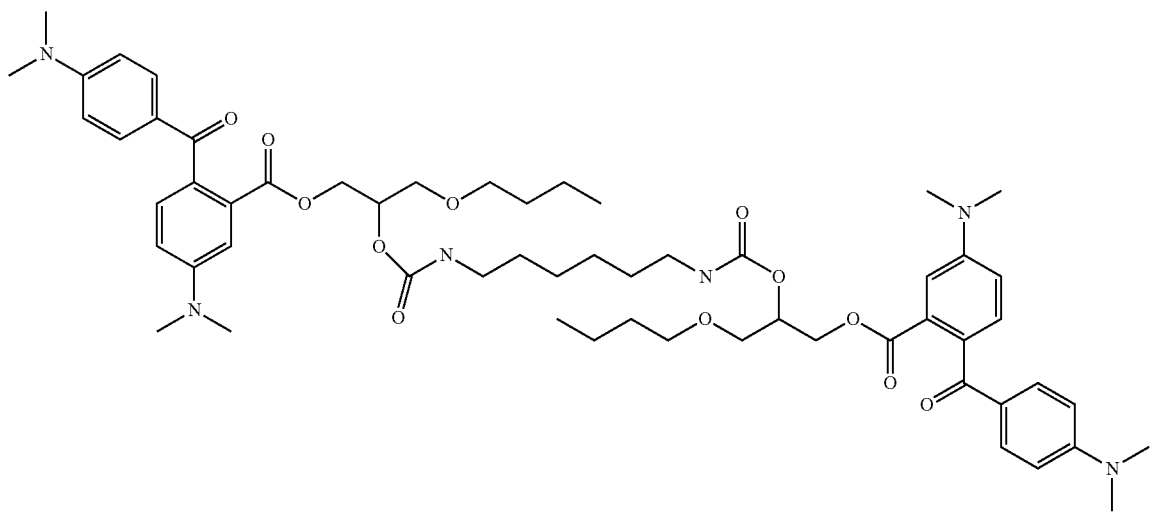

and isomers thereof.

Instead of being esterified, the compounds of Formula II can also be neutralized with a base, giving water soluble materials of Formula Ia:

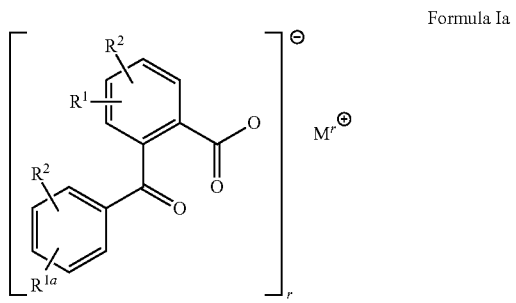

Formula Ia wherein:
R$^1$ and R$^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of R$^1$ and R$^{1a}$ is a tertiary amine;
Each R$^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy;
r denotes an integer from 1-6;
M is selected from the group consisting of a mono-, di-, tri-, tetra-, penta- or hexavalent metal cation, a protonated tertiary amine, tetraalkyl ammonium group radical, phosphonium, sulfonium, and pyridinium, each of which can be optionally substituted by one or more $C_1$-$C_{12}$ alkyl radicals.

The carboxylic acid group in the compounds of Formula II can be partly or completely neutralized to form compounds of Formula Ia, depending on the required solubility in aqueous energy curing systems. As neutralizing agents, metal carbonates, metal hydroxides, metal alkoxides, tetraalkylammoium hydroxides, or strong amines are suitable. Examples include, but are not limited to, potassium carbonate, sodium hydroxide, lithium hydroxide, magnesium hydroxide, potassium hydroxide, tetraethylammonium hydroxide, sodium methoxide, butyl lithium or diazabicyclooctane (DABCO) and tetramethylguanidine. By evaporation of water, the compounds of Formula Ia are obtained as solids salts, which can also crystallize as their hydrate salts.

The aqueous curable compositions of the present invention are made by dissolving, mixing or blending a water soluble, or dispersible, acrylate or methacrylate with compounds of Formula Ia. The weight ratio range of (meth) acrylate compounds and compounds of Formula Ia is from 99.5:0.5 to 50:50, preferred is 95:5 to 85:15. The UV-curable aqueous compositions can be a real solution, or a dispersion or emulsion.

Independently, the compounds of Formula Ia can also be used in non-aqueous UV and LED curing systems, as the large organic part of the molecules provide solubility in polar acrylate and methacrylate monomers as well.

The curable compositions of the present invention are made by dissolving, mixing or blending an acrylate or methacrylate with compounds of Formula I and/or II. The weight ratio range of acrylate or methacrylate compounds and compounds of Formula I and/or II is from 99.5:0.5 to 50:50, preferred is 95:5 to 85:15.

A non-limiting list of examples of acrylates suitable in the radiation curable compositions include ethylene glycol diacrylate, 1,4-butandiol diacrylate, 1,6-hexandiol diacrylate, dipropylene glycol diacrylate, neopentylglycol diacrylate, ethoxylated neopentylglycol diacrylates, propoxylated neopentylglycol diacrylates, tripropylene glycol diacrylate, bisphenol-A diacrylate, ethoxylated bisphenol-A-diacrylates, bisphenol-A-diglycidylether diacrylate, ethoxylated bisphenol-A-diacrylates, poly(ethylene)glycol diacrylates, trimethylolpropane triacrylate, ethoxylated trimethylolpropane triacrylates, propoxylated trimethylolpropane triacrylates, propoxylated glycerol triacrylates, pentaerythritol triacrylate, ethoxylated pentaerythritol triacrylates, propoxylated pentaerythritol tetraacrylates, ethoxylated pentaerythritol tetraacrylates, ditrimethylolpropane tetraacrylate, dipentaerythritol pentaacrylate, dipentaerythritol hexaacrylate or mixtures thereof, and the like. Preferred are ethoxylated trimethylolpropane triacrylates, ethoxylated pentaerythritol triacrylates and propoxylated pentaerythritol tetraacrylates, oligomeric and polymeric acrylates applied in the art, such as for example epoxy acrylates, polyester acrylates, acrylated polyurethanes, acrylated polyacrylates, acrylated polyethers, acrylated epoxidized oils based on linseed oil and soybean oil and mixtures thereof, and the like.

A non-limiting list of examples of suitable methacrylates are ethylene glycol dimethacrylate, 1,4-butandiol dimethacrylate, 1,6-hexandiol dimethacrylate, dipropylene glycol dimethacrylate, neopentylglycol dimethacrylate, ethoxylated neopentylglycol dimethacrylates, propoxylated neopentylglycol dimethacrylates, tripropylene glycol dimethacrylate, bisphenol-A dimethacrylate, ethoxylated bisphenol-A-dimethacrylates, bisphenol-A-diglycidylether dimethacrylate, ethoxylated bisphenol-A-dimethacrylates, poly(ethylene)glycol dimethacrylates, trimethylolpropane trimethacrylate, ethoxylated trimethylolpropane trimethacrylates, propoxylated trimethylolpropane trimethacrylates, propoxylated glycerol trimethacrylates, pentaerythritol trimethacrylate, ethoxylated pentaerythritol trimethacrylates, propoxylated pentaerythritol tetramethacrylates, ethoxylated pentaerythritol tetramethacrylates, ditrimethylolpropane tetramethacrylate, dipentaerythritol pentamethacrylate, dipentaerythritol hexamethacrylate or mixtures thereof, preferably ethoxylated trimethylolpropane trimethacrylates, ethoxylated pentaerythritol trimethacrylates and propoxylated pentaerythritol tetramethacrylates, mixtures thereof, and the like.

Suitable water-soluble or water-dispersible acrylates for the inventive aqueous compositions are, for example, highly ethoxylated multifunctional acrylates such as polyethylene oxide diacrylates or ethoxylated trimethylol propane triacrylates, ethoxylated pentaerythritol triacrylates or epoxy acrylates, such as alkane diglycidylether diacrylates, polyglycerol diacrylates or aqueous acrylated polyurethane acrylate dispersions such as Bayhydrol UV2280 and UV2282 (Trademark of Bayer Company). Especially in combinations with polyurethane acrylates, high curing speeds were observed.

The compounds of Formulae I, Ia and II are useful in radiation curable compositions which can be UV-cured by an actinic light source, such as UV-light, provided by a high-voltage mercury bulb, a medium-voltage mercury bulb, a xenon bulb, a carbon arc lamp, a metal halide bulb, and especially with an UV-LED lamp or sunlight. The wavelength of applied irradiation is preferably within a range of 300 to 500 nm, more preferably 320-395 nm, and most preferably 365 to 395 nm.

Due to the high molar extinction coefficients of compounds of Formulae I, Ia and II, they are especially suitable for printing inks and coatings. The inks are made according to the methods known in the art, as, for example, by dispersing a pigment in the radiation curable compositions of this invention with a bead mill or a three roll mill until the desired particle size and color strength is achieved.

The energy curable inks or coatings may contain one or more colorants in the form of a dye or pigment dispersed therein. Pigments suitable for use in the present invention include conventional organic or inorganic pigments. Representative pigments may, for example, be selected from the group of Pigment Yellow 1, Pigment Yellow 3, Pigment Yellow 12, Pigment Yellow 13, Pigment Yellow 14, Pigment Yellow 17, Pigment Yellow 63, Pigment Yellow 65, Pigment Yellow 73, Pigment Yellow 74, Pigment Yellow 75, Pigment Yellow 83, Pigment Yellow 97, Pigment Yellow 98, Pigment Yellow 106, Pigment Yellow 111, Pigment Yellow 114, Pigment Yellow 121, Pigment Yellow 126, Pigment Yellow 127, Pigment Yellow 136, Pigment Yellow 138, Pigment Yellow 139, Pigment Yellow 174, Pigment Yellow 176, Pigment Yellow 188, Pigment Yellow 194, Pigment Orange 5, Pigment Orange 13, Pigment Orange 16, Pigment Orange 34, Pigment Orange 36, Pigment Orange 61, Pigment Orange 62, Pigment Orange 64, Pigment Red 2, Pigment Red 9, Pigment Red 14, Pigment Red 17, Pigment Red 22, Pigment Red 23, Pigment Red 37, Pigment Red 38, Pigment Red 41, Pigment Red 42, Pigment Red 48:2, Pigment Red 53:1, Pigment Red 57:1, Pigment Red 81:1, Pigment Red 112, Pigment Red 122, Pigment Red 170, Pigment Red 184, Pigment Red 210, Pigment Red 238, Pigment Red 266, Pigment Blue 15, Pigment Blue 15:1, Pigment Blue 15:2, Pigment Blue 15:3, Pigment Blue 15:4, Pigment Blue 61, Pigment Green 7, Pigment Green 36, Pigment Violet 1, Pigment Violet 19, Pigment Violet 23, Pigment Black 7, and the like.

The radiation curable compositions and inks of this invention may contain the usual additives to modify flow, surface tension, gloss, and abrasion resistance of the cured coating or printed ink.

Such additives contained in inks or coatings typically are a surface-active agent, a wax, or a combination thereof. These additives may function as leveling agents, wetting agents, slip agents, dispersants and de-aerators. Preferred additives include fluorocarbon surfactants, silicones and organic polymer surfactants and inorganic materials such as talc. Examples include the Tegorad product lines (Tegorad are trademarks and are commercially available products of Tego Chemie, Essen, Germany) and the Solsperse product lines (Solsperse are trademarks and are commercially available products of Lubrizol company)

The radiation curable composition of the present invention may optionally contain small amounts of additional type-1 and type-2 photoinitiators, such as, for example, benzophenones, benzilketales, dialkoxy acetophenones, hydroxyalkylacetophenones, aminoalkylphenones, acylphosphinoxides and thioxanthones. Examples include, but are not limited to, benzophenone, methylbenzophenone, 4-phenylbenzophenone, 4,4'-bis(dimethylamino)-benzophenone, 4,4'-bis(diethylamino)-benzophenone, 2,2-dimethoxy-2-phenylacetophenone, dimethoxyacetophenone, diethoxyacetophenone, 2-hydroxy-2-methyl-1-phenylpropan-1-one, 2-benzyl-2-dimethylamino-1-(4-morpholinophenyl)-butan-1-one, 2-methyl-1-[4(methoxythio)-phenyl]-2-morpholinopropan-2-one, diphenylacylphenyl phosphinoxide, diphenyl(2,4,6-trimethylbenzoyl) phosphinoxide, 2,4,6-trimethylbenzoylethoxyphenyl phosphinoxide, 2-isopropylthioxanthone, 4-isopropylthioxanthone, 2,4-dimethylthioxanthone and their oligomeric counterparts.

The substrate to be printed on may be composed of any typical substrate material such as paper, plastics, metals, and composites. The substrate may be print stock typically used for publications, or may be a packaging material in the form of a sheet, a container such as a bottle or can, or the like. In most instances, the packaging material is a polyolefin such as a polyethylene or a polypropylene, a polyester such as polyethylene terephthalate, or a metal such as an aluminum foil, a metalized polyester, or a metal container.

The curable compositions of this invention are suitable as UV curable protective coatings, UV-powder coatings, UV-overprint varnishes, UV-lacquers, polymerizable masses for UV-curable 3D printing and prototyping, aqueous coatings and impregnation fluids, curable with UV-light and LED's emitting at wavelengths of preferably 365-405 nm.

The curable inks of the present invention are suitable in virtually any ink or coating system, such as for example a UV-offset ink, a UV-flexographic ink, a UV-jet ink, a UV-gravure ink or a UV-screen ink, curable with UV-light and LED's emitting at wavelengths of preferably 365-405 nm.

The radiation curable compositions of the present invention are especially suitable for such applications in which no small molecules which have the tendency to migrate, or are under suspect to cause health risks, are present. Such applications are, for example, the coating of (food) packaging articles, where especially small photoinitiator molecules are undesirable.

Water-soluble compounds of Formula Ia are especially suitable in environment friendly water-based inks, such as, for example, water-based flexographic inks sold under the trade name "Wetflex" (Sun Chemical corporation), and make them curable with UV and LED light.

Once the energy curable composition is applied and cured to the packaging material, it may be used to contain any kind of liquid or solid material, such as foods, drinks, cosmetics, biological materials or specimens, pharmaceuticals, etc.

The energy curable compositions of this invention may be formulated as inks, adhesives, paints, coatings and the like. The fields of use lie in, but are not limited to, graphic arts, wood coatings, metal coatings, rigid packaging, automotive and automotive refinish paints and coatings, and adhesives. A preferred field of use is in inks and coatings for graphic arts. An especially preferred field of use is in inks and coatings for packaging materials.

EXAMPLES

The following examples illustrate specific aspects of the present invention and are not intended to limit the scope thereof in any respect and should not be so construed.

Test Methods:

Molecular Weight Determination:

Molecular weight was measured by Gel Permeation Chromatography (GPC) using three GPC columns (manufactured by PSS (Polymer Standards Service-USA, Inc.)), SDV 5 μm 1000 Å, SDV 5 μm 500 Å, and SDV 5 μm 100 Å, at a flow rate of 1.0 ml/min. The eluent was tetrahydrofurane (THF), and the column temperature was 40° C. Calibration was done using mono-disperse polystyrene equivalent molecular weight calibration. A differential refractive index detector (RI) and a UV-detector (254 nm) were used. The dispersability (Mw/Mn) was calculated from the measurement results.

UV-Spectra Measurement:

Spectra were acquired using a Unicam UV-2 UV/VIS spectro-photometer. All absorption spectra were obtained using 1 cm cuvettes, scanning within the 200-800 nm range. Solutions were prepared in a 100 $cm^3$ volumetric flask, and, if required, subsequently diluted so that a maximum absorbance of less than 2 was obtained. From the absorption the molar extinction coefficient e was calculated in liter*$mol^{-1}$*$cm^{-1}$.

Melting Point:

Melting points were determined by a calibrated Buchi melting point apparatus.

Viscosity:

Viscosity was measured with a Cone & Plate Physika 300 Rheometer at 25° C. if no different temperature is given in the text (D=2 to 100 $s^{-1}$).

Tack:

Tack was measured with a calibrated "Tack-o-scope" (1 ml ink at 30° C. held for 90 seconds at 50 rpm, then 30 seconds at 300 rpm). Then, the tack value was taken at 150 rpm.

FTIR Spectra Measurement:

The Fourier transform infrared (FTIR) spectra were recorded on a Bio-Rad Excalibur FTS 3000 spectrophotometer using a surface reflectance method (solid samples, Golden Gate single reflection diamond attenuated total reflectance accessory).

Assessment of Cure:

a) Film hardness: The thumb was pressed on the surface of the cured coating and rotated for 90°. If no marks were left on the surface, the cure was regarded as 1, or sometimes as "ok", and failures are rated in 5 steps to 5. A rating of 5 means that the surface was cracked.

b) Solvent resistance: Higher crosslinked materials pose a better resistance to solvents. A cotton tipped plastic stick was soaked with acetone or alcohol and rubbed over the cured coating or ink. The more rubs the cured coating or ink withstands without being destroyed, the better rated the cure is. Acetone is typically more aggressive than alcohol.

c) Set-off test: Prints of UV-cured samples, which were printed with a comparable density, were covered with a white counter paper. Then, with a pressure of 10 tons, the printed substrate and the counter paper were pressed together. Then, the counter paper was removed from the print and the amount of transferred ink on the counter paper was measured by a densitometer. As a rule, the lower the amount of transferred ink, the lower the readings on the densitometer, and the better the cure.

Example 1

Synthesis of phthalide intermediate 3-(4-Dimethylaminophenyl)-6-dimethylaminophthalid A 3-necked 2-liter-flask equipped with a mechanical stirrer, reflux condenser, and inner thermometer was charged with 306 g (283 ml, 3.0 mole) acetic acid anhydride, 210 g (200 ml, 3.5 mole) acetic acid, 298 g (2.0 mole) 4-dimethylamino benzaldehyde and 386 g (2.33 mole) of 3-dimethylamino benzoic acid. The mixture was stirred and heated to reflux for approximately four hours. A dark colored mixture was obtained which was allowed to cool to 68° C. and was diluted with 700 ml methanol. The mixture was stirred thoroughly and heated to reflux for one hour, resulting in a homogenous mixture.

Then, the mixture was cooled to 15° C. using an ice-bath, and a precipitate was filtered and washed with cooled (15° C.) methanol. The purple color disappeared. The resulting white solid was suspended in 400 ml cold methanol (10-15°

C.), stirred thoroughly, filtered, and washed again. The obtained ivory-white solid was dried in vacuum.

Yield: 480.2 g

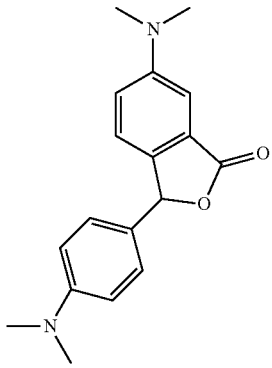 [SMILES: CN(C)c1ccc(C2OC(=O)c3cc(N(C)C)ccc32)cc1]

Characterization:

Melting point: 187° C.

FT-IR-spectroscopy (cm$^{-1}$): 2886 (br); 2810 (w); 1736 (vs); 1612 (s); 1516 (s); 1441 (w); 1354 (s); 1276 (m); 1215 (w); 1053 (s); 946 (s); 807 (s)

Mass Spectroscopy (m/z) 296, 251, 235, 208 (100%), 192, 165, 148, 125, 103, 77, 63, 44, 28

Example 2

5-(dimethylamino)-2-[4-(dimethylamino)benzoyl]-benzoic acid (Compound of Formula II)

A 500 ml 3-necked flask equipped with a mechanical stirrer, reflux condenser and thermometer was charged with 50.0 g (0.169 mole) 3-(4-dimethylaminophenyl)-6-dimethylaminophthalide of Example 1. The ivory white solid was suspended in 200 ml of a 10 wt % aqueous solution of sodium hydroxide. The resulting mixture was heated to 90° C. for one hour with stirring, to obtain a homogenous mixture. Then, 50.0 g (0.222 mole) of sodium 3-nitrobenzenesulfonate was added to the solution, and the reddish mixture was refluxed for 15 hours on an oil bath (temperature 110-115° C.) resulting in a dark-colored mixture.

After cooling, the pH of the solution was adjusted to 4 with about 100 ml of a 50 wt % aqueous solution of acetic acid to precipitate a yellow solid. The solid was collected by filtration and dissolved in a saturated aqueous solution (100 ml) of sodium carbonate. Insoluble material was removed by filtration and the pH of the filtrate was adjusted to 5 to 6 with aqueous acetic acid to precipitate a yellow solid. The solid was collected by filtration and re-crystallized from 130 ml ethanol. An intense yellow solid was collected, which was soluble in DMSO.

Yield: 33 g (63% after re-crystallization)

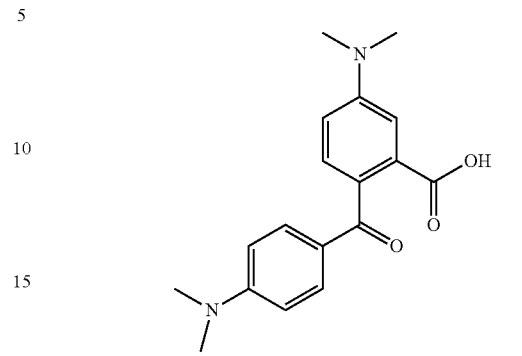

Characterization:

Melting point: 269-272° C.

Acid value: 177 mg KOH/g

FT-IR-spectroscopy (cm$^{-1}$): 1670 (s); 1590 (vs); 1526 (w); 1370 (m); 1289 (s); 1234 (w); 1074 (w); 941; 814

Mass Spectroscopy (m/z): (with MSTFA for derivatization): 384 (M$^{·+}$+TMS), 369, 295, 264, 207, 148 (100%), 73, 44, 28

Example 3

2-(3,4-dimethoxybenzoyl)-5-(dimethylamino)benzoic acid (Compound of Formula II)

25.0 g of 3-(3,4-dimethoxyphenyl)-6-dimethylaminophthalid was stirred in 150 ml of aqueous potassium hydroxide solution (9% in strength). Then, the mixture was heated to 95° C. until a clear solution was obtained. To the solution, 25.0 g of nitrobenzenesulfonate sodium salt was added in portions, and the mixture was heated under reflux for 12 hours. Then the mixture was allowed to cool down to room temperature, and adjusted to pH=4 with acetic acid, upon which the reduced oxidant precipitated. The precipitate was separated by filtration and the solution was adjusted to pH=6-7, and a yellow solid precipitated, which was filtered and washed. Re-crystallization from ethanol gave pale yellow crystals.

Yield: 20.1 g

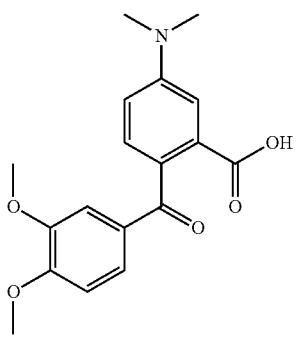 [SMILES: COc1ccc(C(=O)c2ccc(N(C)C)cc2C(=O)O)cc1OC]

Characterization:

Acid value: 165 mg KOH/g

Melting point: 238-241° C.

Example 4

Synthesis of 5-(dimethylamino)-2-[4-(dimethylamino)benzoyl]-benzoic acid with butylglycidyl ether (an ester compound of Formula I)

To a mixture containing 31.2 g (0.1 mole) 5-(dimethylamino)-2-[4-(dimethylamino)benzoyl]-benzoic acid from Example 2 and 13.1 g (0.1 mole) butylglycidyl ether, 400 mg triphenylphosphine (TPP, 9000 ppm) was added. Then, the mixture was heated to 110-124° C. until the acid value no longer decreased (about 8 hours). In the course of the reaction, the intense yellow mixture turned brownish and more clear. The crude reaction product was diluted with 15 ml ethyl acetate and stirred for ten minutes. Insoluble starting material was removed by filtration. The crude product was obtained as a clear, brown liquid in ethyl acetate.

Residual solvent was removed using a rotary evaporator. The compound was further dried in vacuum.
Yield: 39.2 g (brownish, clear, viscous liquid)

Characterization:
Acid value: <2 mg KOH/g
FT-IR-spectroscopy (cm$^{-1}$): 3431 (br), 2924 (br, sh), 2866 (br), 1721, (m), 1586 (vs), 1539 (m), 1431 (w), 1361 (s), 1293 (s), 1242 (s), 1151 (vs), 1060 (s), 927 (m), 826 (m), 763 (s) Gas-chromatography: (two signals of both possible products after opening of the epoxy-ring ratio 17:83 MS of main product after derivatization with N-methyl-N-(trimethylsilyl)trifluoroacetamide (MSTFA)
Mass Spectroscopy (m/z): 515 (M$^{+\bullet}$+TMS), 352, 323, 311, 295 (100%), 279, 267, 251, 224, 148, 73

Example 5

Compound of Formula I 31.3 g (0.1 mole) of 5-(dimethylamino)-2-[4-dimethylamino] benzoylbenzoic acid from Example 2 was mixed with 101.0 g (0.50 mole) of a 1:1 mixture of butane diol diglycidylether and butane diol monoglycidylether and 1.3 g of triphenylphosphine. The mixture was heated to 150° C. for 3 hours. At that time the acid value dropped below 4 mg KOH/g. Then, the excess of butane diol glycidylethers was distilled off under vacuum of 0.1 hPa. A brown highly viscous liquid remained.
Yield: 41.1 g (49% mono & 51% di-functional product)
Characterization:
Acid value: 3 mg KOH/g
Molecular weight: Mn=410, Mw=610
(butane-1,4-diylbis(oxy))bis(2-hydroxypropane-3,1-diyl) bis(5-(dimethylamino)-2-(4-(dimethylamino)benzoyl) benzoate)

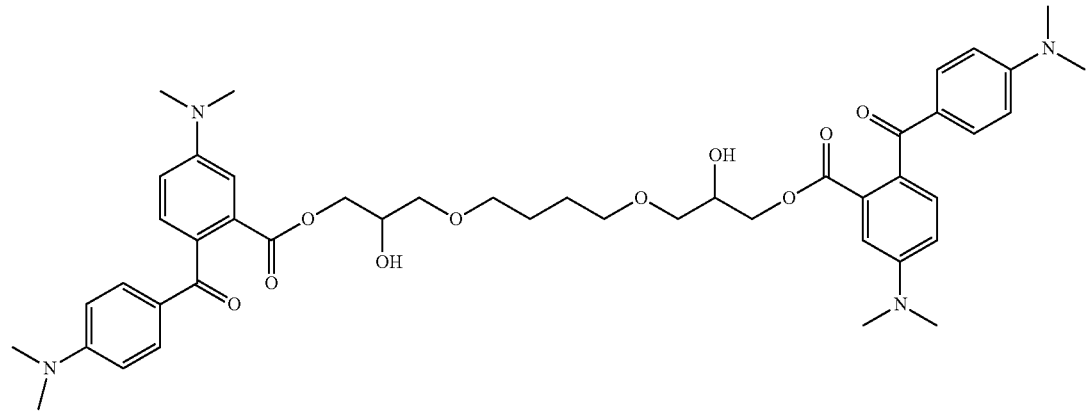

2-hydroxy-3-(4-hydroxybutoxy)propyl 5-(dimethylamino)-2-(4-(dimethylamino)benzoyl)benzoate

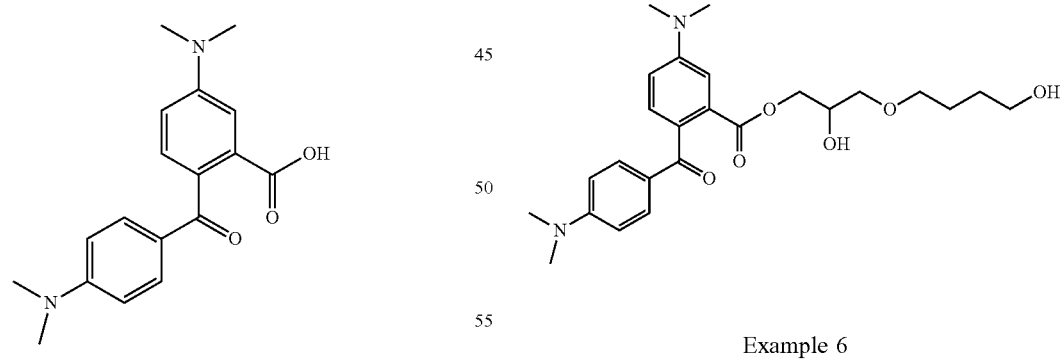

Example 6

5-(dimethylamino)-2-[4-(dimethylamino)benzoyl]-benzoic acid potassium salt (Compound of Formula Ia)

31.2 g (0.1 mole) of 5-(dimethylamino)-2-[4-(dimethylamino)benzoyl]-benzoic acid from Example 2, was dispersed in 100 ml water. The acid was neutralized by dropwise addition of an aqueous solution of potassium hydroxide (10 wt. %). After addition of 56 g of KOH the yellow suspension turned into a clear brown-greenish solution. The mixture was allowed to stir for 30 minutes and turned turbid yellow. An aliquot was titrated against phenolphthalein to determine the needed amount of potassium hydroxide solution for neutralization. The calculated amount of potassium hydroxide solution was added drop-wise to the reaction mixture, resulting in an intense green clear mixture. The reaction mixture was stirred for 30 minutes at room temperature without change in color. The pH-value was determined to be 8. Water was removed using a rotary evaporator. The resulting reaction product crystallized from the crude reaction mixture.

The product was purified by precipitation: a highly concentrated solution of the product in water was added drop-wise to a stirred surplus of THF. The product precipitated and was collected by filtration.

The product showed good solubility in water and limited solubility in methylene chloride.

Yield: 33.0 g (0.094 mole, 94%) pale yellow crystals

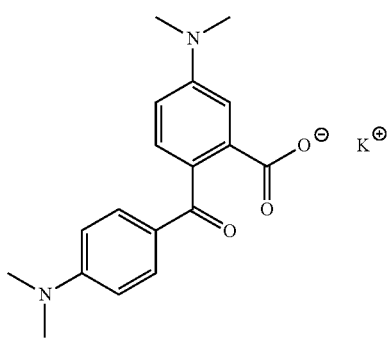 [SMILES: CN(C)c1ccc(C(=O)c2ccc(N(C)C)cc2C(=O)[O-])cc1 ; [K+]]

Characterization:

Acid value: <2 mg KOH/g

Melting point: 140° C.-145° C.

FT-IR-spectroscopy (cm$^{-1}$): IR: 2885 (br); 2810 (br); 1562 (vs); 1423 (w); 1363 (s); 1291 (vs); 1142 (s); 1063 (m); 927 (m); 870 (w); 810 (m); 764 (s)

UV-spectroscopy: λmax (H$_2$O): 365 nm

Molar extinction coefficient: 36192 liter*mol$^{-1}$*cm$^{-1}$

FIG. 1 shows the characterization of the UV absorption spectrum of Example 6. The UV-absorption spectrum of the compound of Example 6 shows that the chromophor has the ability to absorb the strongest emission wavelength from medium pressure mercury arc lamps at 365 nm. Moreover, the absorption UV-absorption spectrum fits very well to the wavelengths emitted by typical commercially available LED bulbs at 365, 385, 395 and 405 nm.

Example 7

LED-Curing Aqueous Solution with a Compound of Formula Ia from Example 6

7.0 g of acrylate resin Sartomer CN 132 (Cray Valley Company) was placed in a beaker. The resin was diluted with 1.0 g of de-ionized water. Then, 0.5 g of 5-(dimethyl-amino)-2-[4-dimethylamino] benzoylbenzoic acid potassium salt from Example 6 dissolved in 2 ml of de-ionized water was added under stirring. A yellowish stable aqueous solution was obtained, which was applied on a coated "Byk" cardboard test chart with a wire applicator (6 μm wet) and cured with a Phoseon LED bulb (8 W at 395 nm).

TABLE 1

| Example 7 cure results | | |
|---|---|---|
| | Conveyor speed of LED-curing rig [meter/min] | |
| | 9 | 13 |
| Hardness - Thumb twist test | ok | ok |
| Solvent resistance - Isopropanol rubs | >40 | ~40 |
| Solvent resistance - Acetone rubs | >30 | ~10 |

Table 1 shows the curing performance of an aqueous LED-curing solution at two different conveyor speeds. The higher the conveyor speed, the less is the dose of UV-light. Table 1 shows that at a conveyor speed of 9 meter/min films are obtained with good hardness and with high solvent resistance. At a speed of 13 meter/min the resistance of the LED-curable varnish to acetone is reduced.

Example 8

LED-Curing Aqueous Dispersion with a Compound of Formula Ia from Example 6

20.0 g of acrylated polyurethane dispersion Bayhydrol UV 2280 (39% solids, Bayer company) was placed in a beaker. Then, 2 g of aliphatic epoxy acrylate Laromer 8765 (BASF company) was added. Then, 0.6 g of 5-(dimethyl-amino)-2-[4-dimethylamino]benzoylbenzoic acid potassium salt from Example 6 was added under stirring. A yellowish stable dispersion was obtained, which was applied on a coated "Byk" cardboard test chart with a wire applicator (10 μm wet) and cured with a Phoseon LED bulb (8 W at 395 nm).

TABLE 2

| Example 8 cure results | | |
|---|---|---|
| | Conveyor speed of LED-curing rig [meter/min] | |
| | 10 | 20 |
| Hardness - Thumb twist test | ok | ok |
| Solvent resistance - Isopropanol rubs | >50 | ~40 |
| Solvent resistance - Acetone rubs | >30 | ~10 |

Table 2 shows the curing performance of an aqueous LED-curing dispersion at two different conveyor speeds. The higher the conveyor speed, the less is the dose of UV-light. Table 2 shows that at a conveyor speed of 10 meter/min films are obtained with good hardness and with high solvent resistance. At a speed of 20 meter/min the resistance of the LED-curable varnish to acetone is reduced.

Example 9

LED-Module (365 nm) Curable Composition with a Compound of Example 4

9.0 g of a compound prepared as described in Example 4 was dissolved in 89.0 g alkoxylated pentaerythritol tetraacrylate (PPTTA, e.g. SR494LM of Sartomer, France) by stirring at 60° C. for about 30 minutes. To the yellow, clear, low viscous solution 2.0 g Omnipol BP (commercially available from IGM Resins B. V., Waalwijk, NL) was added. A clear, yellow solution was obtained.

The curable composition was applied on a coated "Byk" cardboard test chart with a wire applicator (6 μm) and cured with a Heraeus Noblecure UV-LED module as described below (8.0 W at 365 nm, and 4.6 W at 365 nm).

The curing experiment was done at the measuring laboratory of Heraeus Noblelight GmbH in Hanau, Germany. As the LED-module, a Heraeus Noblecure (registered trademark of Heraeus Noblelight GmbH, Hanau, Germany) UV-LED module operating at a wavelength of 365 nm with 8 W/cm$^2$ at 100% was used. The module can be dimmed to work also with lower emittance.

The power (emittance) of the UV-LED module was measured by a UV-sensor NobleProbe (registered trademark of Heraeus Noblelight GmbH, Hanau, Germany), a special measuring instrument for UV-LEDs commercially available from Heraeus Noblelight GmbH. It can be used to take precise measurements of irradiance in the near UV range from 1 mW/cm$^2$ to 100 W/cm$^2$ at wavelengths of between 360 nm and 450 nm.

The UV-LED measuring instrument was calibrated in Heraeus Noblelight's own accredited measuring laboratory. However, the NobleProbe instrument just gives a value for the emittance of the UV-LED module, not a dose. So it is independent of the belt-speed. Therefore, the dose (which depends on the belt speed) was measured using a Power Puck II of EIT (Electronic Instrumentation &Technology, Inc.; EIT Instrument Markets Group, Sterling, USA). The Power Puck gives the measured irradiance at 365 nm as a value in the UV-A region.

Belt-speed was 12.7 m/min in both experiments. Distance between substrate (paper-board) and the LED-bulb was 2.2 cm. First, we used the LED-module at 100% and then we dimmed the LED to 50%. The measured values are summarized in the table 3.

TABLE 3

Details about the LED module used to cure Example 9

|  | 365 nm LED-module | 365 nm LED-module |
|---|---|---|
| Intensity of Module [%] | 100 | 50 |
| Belt-speed [m/min] | 12.7 | 12.7 |
| Distance between board and module [cm] | 2.2 | 2.2 |
| Irradiance [W/cm$^2$] (measured with NobleProbe) | 8.0 | 4.6 |
| UV-Dose [mJ/cm$^2$] measured with PowerPuck II | 976 | 509 |

TABLE 4

Example 9 cure results

|  | 365 nm LED-module (100%) | 365 nm LED-module (50%) |
|---|---|---|
| Film Hardness: Thumb twist test | OK | Ok (very slight mark of fingerprint visible) |
| Solvent resistance - Acetone double rubs | >25 | >25 |

The results show that the inventive photoinitiator of Example 9 is suitable for LED-curing at 365 nm.

Example 10

Low Migration LED-Photoinitiator with Good Solubility in Acrylates 30.0 g (0.068 mol) of the product as obtained in Example 4 was heated to 80° C. in a 4 necked round bottom flask with mechanical stirrer, inner-thermometer, reflux-condenser and dropping-funnel. Under stirring, 5.5 ml (5.78 g, 0.034 mol) hexamethylene-diisocyanate was added dropwise and the brownish reaction mixture was stirred at 80° C. for 4 hours. Consumption of the isocyanate was monitored by IR-spectroscopy (characteristic band at 2250-2300 cm-1 disappears). If residues of isocyanate were detected by IR-Spectroscopy, it was possible to react residual isocyanate with 0.4 g PEG-600 poly(ethylene glycol)-600 (available from Sigma-Aldrich) by stirring the reaction mixture at 80° C. for 1 hour. Then, conversion of all isocyanate was checked by IR-spectroscopy again.

Yield: 35 g (brown, clear material. Highly viscous liquid at 35° C.)

GPC:

Mn: 1050 Da, Mw 1360 Da

IR: ν [cm-1]: 3318, 2930, 2861, 1716 (s), 1641, 1590 (vs), 1525, 1450, 1364, 1284, 1228, 1146, 1068, 927, 826, 770

Solubility:

The product as obtained according to Example 10 was added to different multifunctional acrylates to check solubility. Propoxylated pentaerythritol tetraacrylate (SR 494 LM, Sartomer company) (PPTTA), trimethylol propane triacrylate (SR 351M, Sartomer company) (TMPTA) and ethoxylated trimethylol propane triacrylate (Ebecryl LEO 10501, Allnex company) (EO-TMPTA) were used. The compound of example 10 was added in amounts of 10 and 20 weight % to each of the acrylates and stirred for 10 minutes at 45° C. In all cases (even at 20 weight %), clear, intense yellow, transparent mixtures were obtained. This shows the very good solubility of the inventive compound.

Example 11

Formulation of an Offset Printing Ink Containing the New LED-Photoinitiator and Assessment of Cure A photo-initiator blend containing no small molecules, and therefore in particular suitable for low migration applications, was prepared by mixing compounds in the weight-ratios given in table 5 at 65° C. In the inventive blend all Omnipol TX was replaced by the inventive compound synthesized as described in Example 10.

TABLE 5

Photoinitiator blend for a low migration ink

|  | Inventive | Comparison |
|---|---|---|
| Omnipol TX |  | 20 |
| Compound from Example 10 | 20 |  |
| 2-Benzyl-2-(dimethylamino)-4'-morpholinobutyrophenone (e.g. Irgacure 369) | 15 | 15 |
| Oligomeric aromatic amine synergist | 20 | 20 |
| Oligomeric benzophenone | 45 | 45 |

Offset Printing Ink Containing the Inventive LED-PI:

The photoinitiator blend according to Table 5 (9.0 wt-%) was in each case mixed with 91.0 (wt-%) of a cyan offset ink containing no photoinitiator blend: SunBeam ELM25 Process Cyan ink (an ink curable by electron beam intended for low migration applications commercially available from Sun Chemical Corporation) using a butterfly stirrer (e.g a tri-foil butterfly stirrer) at a speed of 1500 rpm for 10 minutes. During mixing temperature increased to 47° C.

The inks were printed onto Invercoat G paper, using an IGT C5 proofer to densities of 1.4 to 1.5 (cyan), and cured using a Phoseon LED-module (8 W at 395 nm, at 100% intensity, dimmable).

Intensity of the LED-module was lowered so that the value measured in the UV-V region with Power Puck II was 60 mJ/cm² at a conveyer speed of 10 meter/min, to prevent both inks from full-cure. The conveyor speed of the LED-curing rig was adjusted to 10 meter/min. The resulting UV-dose of the LED-module was measured using a Power Puck II of EIT (Electronic Instrumentation &Technology, Inc.; EIT Instrument Markets Group, Sterling, USA). The Power Puck gives the measured irradiance at 395 nm mainly as a value in the UV-V region. The value measured in the UV-V region for this curing experiment was 60 mJ/cm².

TABLE 6

Properties of inks

|  | Inventive ink | Comparison ink |
| --- | --- | --- |
| Viscosity at 50 s⁻¹, 23° C. (Pa · s) | 54.7 | 41.3 |
| Tack 150 | 250 | 232 |
| LED Cure evaluation |  |  |
| Optical density | 1.43 | 1.45 |
| Film weight (g/m²) | 0.86 | 0.88 |
| Thumb twist (through cure, rating: 1: very good to 5: bad | 3 | 5 |
| Set-off test | 0.29 | 0.40 |

This example shows that the low-migration LED-photoinitiator of the present invention is at least as reactive as Omnipol TX, a commercially available photoinitiator based on thioxanthone chemistry.

The present invention has been described in detail, including the preferred embodiments thereof. However, it will be appreciated that those skilled in the art, upon consideration of the present disclosure, may make modifications and/or improvements on this invention that fall within the scope and spirit of the invention.

What is claimed is:

1. A compound of Formula I:

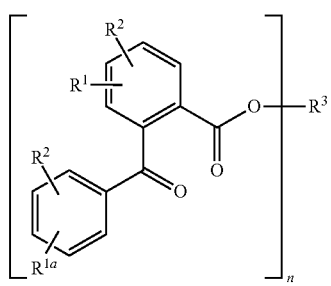

Formula I wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine;

Each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy;

$R^3$ is selected from the group consisting of a mono-, di-, tri-, tetra-, penta-, hexa-, or polyvalent alkyl or alkoxy radical, optionally substituted with one or more independently selected oxygen, sulfur, nitrogen, OH, carbonyl, (hydroxyl)alkyl, COOH, (carboxy)alkyl, $R^4$, carboxamido, (carboxamido)alkyl, or $OCONR^5$;

$R^4$ is selected from the group consisting of $C_3$-$C_{12}$ cycloalkyl, (cycloalkyl)alkyl, $C_6$-$C_{12}$ aryl, $C_3$-$C_{12}$ heterocycle, $C_6$-$C_{12}$ heteroaryl, aralkyl, and alkaryl, each of which is optionally substituted with one or more independently selected OH, (hydroxy)alkyl, $C_1$-$C_{12}$ alkyl, carboxamido, (carboxamido)alkyl, COOH, or (carboxy)alkyl;

$R^5$ is selected from the group consisting of H, $C_1$-$C_{12}$ alkyl, and $C_1$-$C_{12}$ alkoxy; and n denotes an integer from 1-100; provided that n is less than or equal to the valency of the alkyl or alkoxy radical of $R^3$.

2. A compound of claim 1, wherein $R^1$ and $R^{1a}$ are each an independently selected tertiary amine.

3. A compound of Formula Ia:

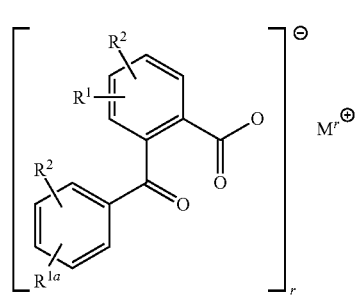

Formula Ia wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine;

Each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy;

r denotes an integer from 1-6;

M is selected from the group consisting of a mono-, di-, tri-, tetra-, penta- or hexavalent metal cation, a protonated tertiary amine, tetraalkyl ammonium group radical, phosphonium, sulfonium, and pyridinium, each of which can be optionally substituted by one or more $C_1$-$C_{12}$ alkyl radicals.

4. A compound of claim 3 wherein $R^1$ and $R^{1a}$ are each an independently selected tertiary amine.

5. A UV-curable ink or coating composition comprising at least one acrylate or methacrylate compound and at least one compound of claim 1.

6. The UV-curable ink or coating composition of claim 5, further comprising at least one colorant.

7. A UV-curable ink or coating composition comprising at least one acrylate or methacrylate compound, at least one compound of claim 3, and optionally water.

8. The UV-curable ink or coating composition of claim 7, further comprising at least one colorant.

9. A UV-curable ink or coating composition according to claim 5, that is curable with LED light having a wavelength maximum of 300 to 450 nm.

10. A UV-curable ink or coating composition according to claim 7, that is curable with LED light having a wavelength maximum of 300 to 450 nm.

11. The compound of claim 1, selected from the group consisting of:

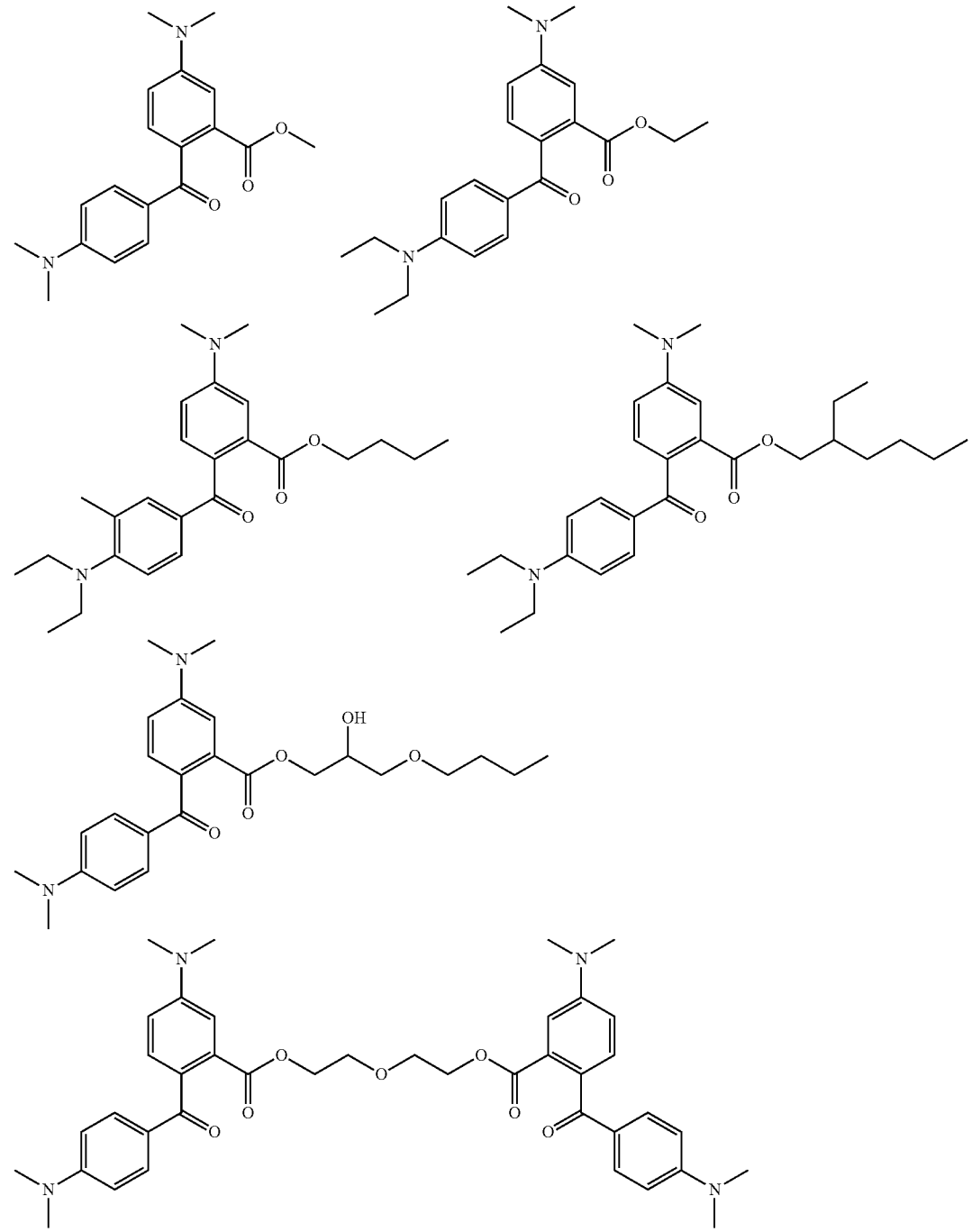

-continued
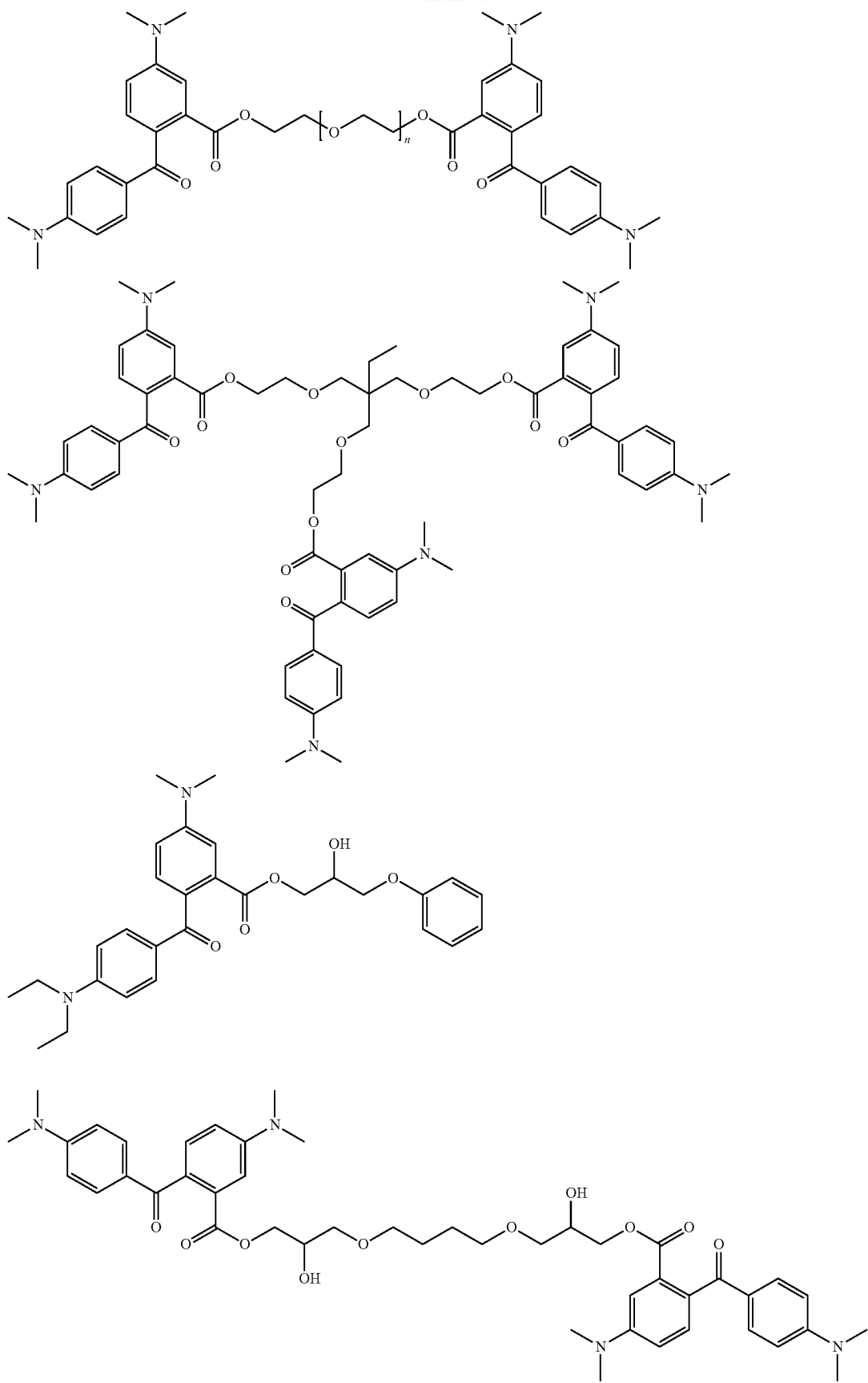

-continued
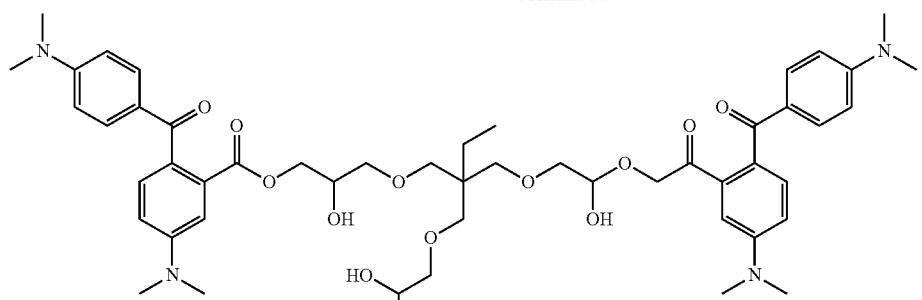
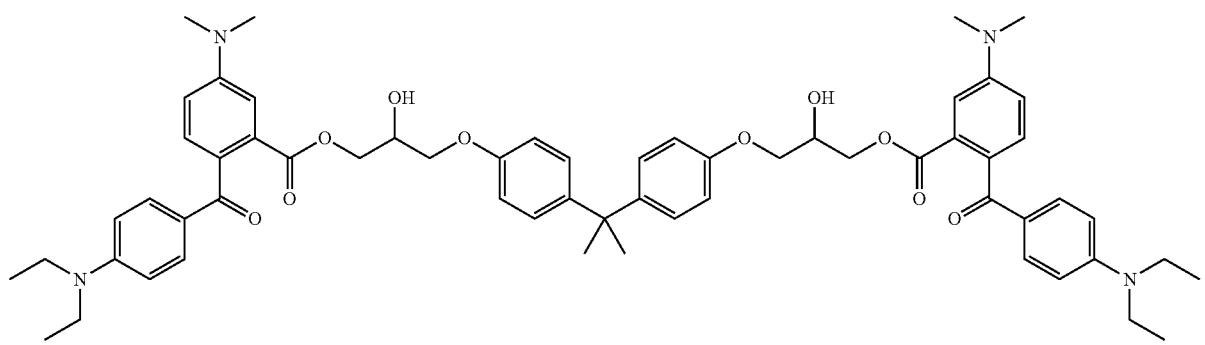
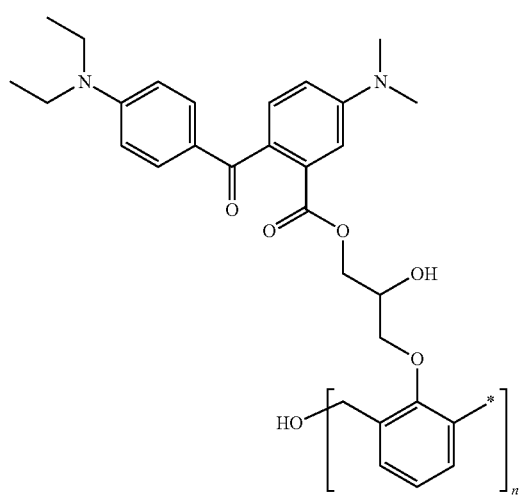

-continued

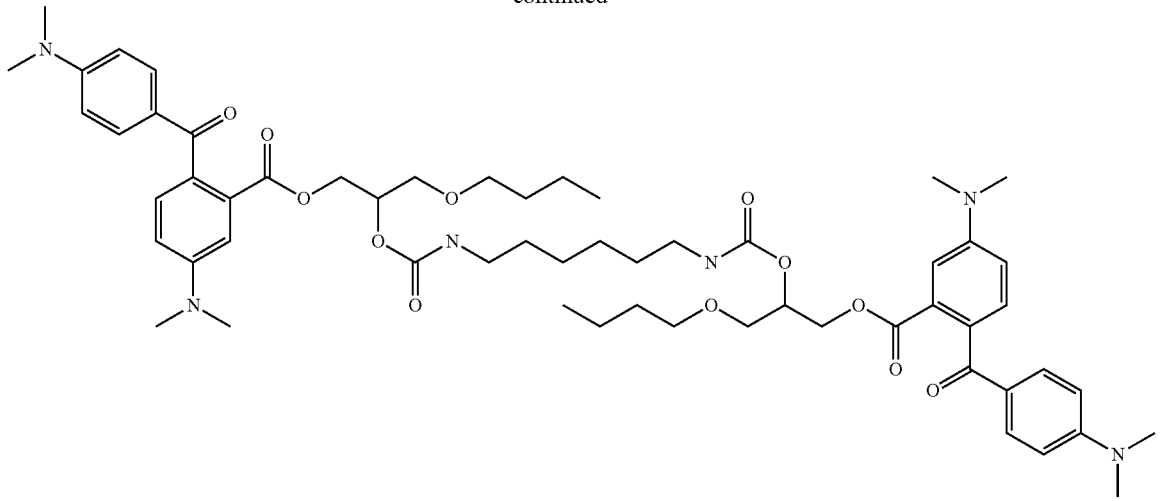

wherein n denotes an integer from 1 to 100.

12. A method of preparing a UV-curable ink or coating composition comprising adding to the ink or coating composition:
a) a photoinitiator compound of Formula II:

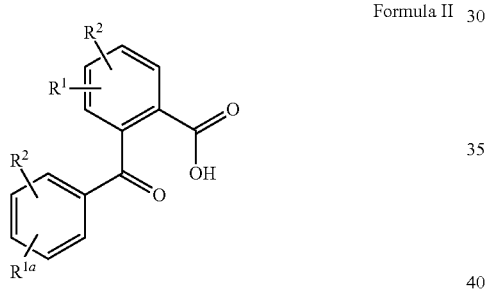

Formula II wherein:
$R^1$ and $R^{1a}$ are each independently selected from the group consisting of tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy; provided that at least one of $R^1$ and $R^{1a}$ is a tertiary amine; and
each $R^2$ is independently selected from the group consisting of hydrogen, a tertiary amine, $C_1$-$C_{12}$ alkoxy, $C_1$-$C_{12}$ alkyl, $C_3$-$C_{12}$ cycloalkyl, and $C_6$-$C_{12}$ aryl radical, each of which is optionally substituted with one or more independently selected oxygen, nitrogen, sulfur, or $C_1$-$C_{12}$ alkoxy,
b) at least one acrylate or methacrylate compound; and
c) optionally, a colorant.

13. The method of claim 12, wherein $R^1$ and $R^{1a}$ of the photoinitiator compound of Formula II are each an independently selected tertiary amine.

14. The method of claim 12, wherein the photoinitiator compound of Formula II is an ester, thioester, urethane, or amide linked compound, absorbing wavelengths in a range of 300-450 nm.

15. The method of claim 12, wherein the photoinitiator compound of Formula II is selected from the group consisting of:
5-(methyl)-2-[4-dimethyl amino] benzoylbenzoic acid;
5-(diethylamino)-2-[4-methyl] benzoylbenzoic acid;
5-(diethylamino)-2-[2-methoxy] benzoylbenzoic acid;
5-(ethoxy)-2-[4-dimethylamino] benzoylbenzoic acid;
5-(dimethylamino)-2-[4-dimethylamino] benzoylbenzoic acid;
5-(dimethylamino)-2-[2-dimehtylamino] benzoylbenzoic acid;
5-(diethylamino)-2-[4-diethylamino] benzoylbenzoic acid;
5-(diethylamino)-2-[2-diethylamino] benzoylbenzoic acid;
5-(dipropylamino)-2-[4-dipropylamino] benzoylbenzoic acid;
5-(morpholino)-2-[4-dimethylamino] benzoylbenzoic acid;
5-(morpholino)-2-[4-morpholino] benzoylbenzoic acid;
5-(dimethylamino)-2-[4-methoxy] benzoylbenzoic acid;
5-(ethoxy)-2-[4-dimethylamino] benzoylbenzoic acid;
5-(aminomethylphenyl)-2-[4-dimethyl amino] benzoylbenzoic acid;
5-(dimethylamino)-2-[4-methylphenylamino] benzoylbenzoic acid;
5-(dimethylamino)-2-[4-dimethylamino] benzoylbenzoic acid;
5-(dimethylamino)-2-[4-methoxyphenyl] benzoylbenzoic acid;
5-(ethoxy)-2-[4-dimethylamino-2-methoxy] benzoylbenzoic acid;
5-(dimethylamino)-2-[4-dimethylamino-2-methoxy] benzoylbenzoic acid;
5-(dimethylamino)-2-[4-methyl-2-methoxy] benzoylbenzoic acid;
5-(dimethylamino)-2-[4-dimetylamino-2-methoxy] benzoylbenzoic acid; and
5-(dimethylamino-3-methyl)-2-[4-methoxy-2-methoxy] benzoylbenzoic acid.

* * * * *